(12) United States Patent
Babudri et al.

(10) Patent No.: US 8,461,354 B2
(45) Date of Patent: Jun. 11, 2013

(54) ORGANIC THIN FILM TRANSISTORS COMPRISING THIENYL OLIGOMERS AND THEIR USE AS GASEOUS PHASE SENSORS

(75) Inventors: Francesco Babudri, Bari (IT); Gianluca Maria Farinola, Bari (IT); Francesco Naso, Bari (IT); Francesco Palmisano, Bari (IT); Luisa Torsi, Bari (IT); Maria Cristina Tanese, Bari (IT); Pier Giorgio Zambonin, Bari (IT); Omar Hassan Omar, Sesto Fiorentino (IT); Ludovico Valli, Lecce (IT)

(73) Assignee: Universita' Degli Studi di Bari, Bari (IT)

( * ) Notice: Subject to any disclaimer, the term of this patent is extended or adjusted under 35 U.S.C. 154(b) by 710 days.

(21) Appl. No.: 12/524,017

(22) PCT Filed: Feb. 6, 2008

(86) PCT No.: PCT/IB2008/000263
§ 371 (c)(1),
(2), (4) Date: Feb. 2, 2010

(87) PCT Pub. No.: WO2008/096239
PCT Pub. Date: Aug. 14, 2008

(65) Prior Publication Data
US 2010/0140597 A1   Jun. 10, 2010

(30) Foreign Application Priority Data

Feb. 7, 2007 (IT) ................. MI2007A0217

(51) Int. Cl.
*C07D 333/78* (2006.01)
(52) U.S. Cl.
USPC ............................................. 549/41
(58) Field of Classification Search
USPC ............................................. 549/41
See application file for complete search history.

(56) References Cited

U.S. PATENT DOCUMENTS
2005/0040394 A1   2/2005   Wu

FOREIGN PATENT DOCUMENTS
EP    1605007 A    12/2005
WO    2004022714 A    3/2004
WO    2005030828 A    4/2005

*Primary Examiner* — Taofiq A Solola
(74) *Attorney, Agent, or Firm* — Hess Patent Law Firm LLC; Robert J. Hess

(57) ABSTRACT

This invention pertains to gaseous analytes sensor devices comprising organic thin film transistor and, in particular, sensors able to perform the enantiomeric discrimination of gaseous analytes.

13 Claims, 8 Drawing Sheets

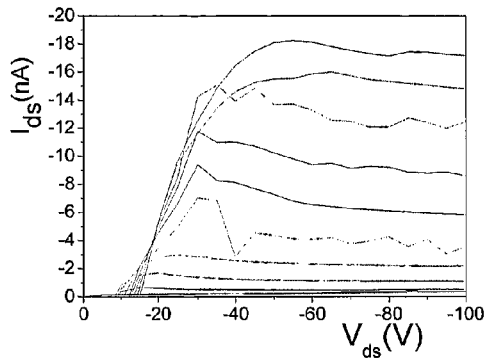
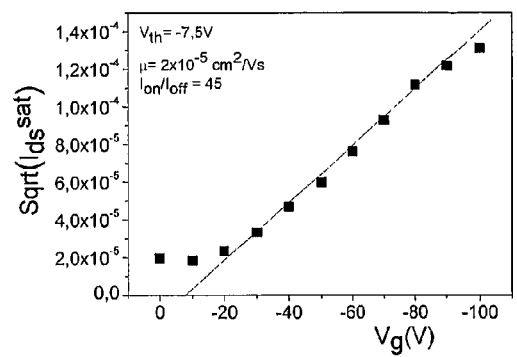
Fig. 6A　　　　　　　　Fig. 6B
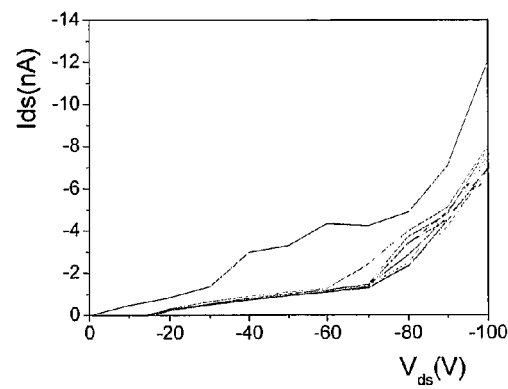
Fig. 7

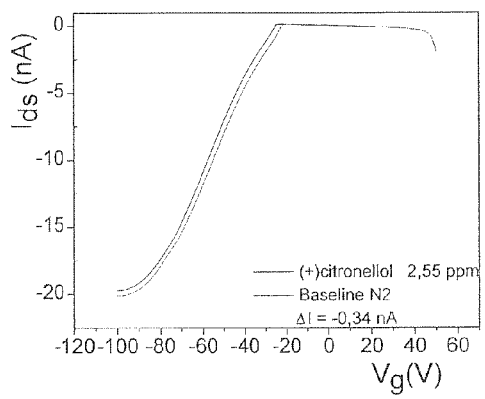
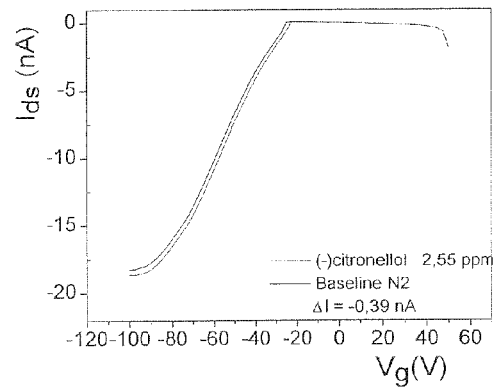
Fig. 13A          Fig. 13B
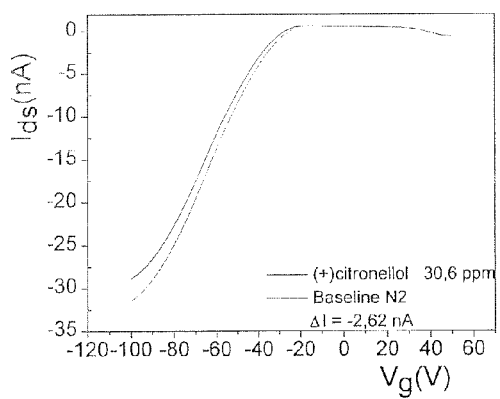
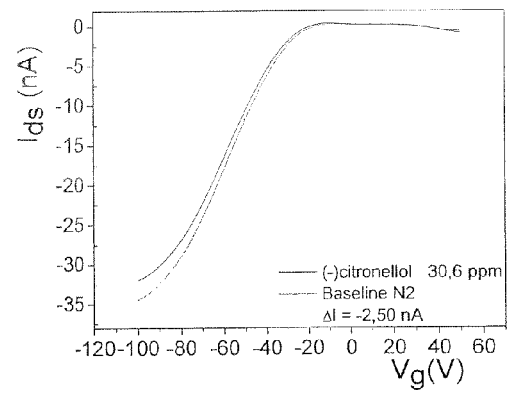
Fig. 13C          Fig. 13D

ORGANIC THIN FILM TRANSISTORS COMPRISING THIENYL OLIGOMERS AND THEIR USE AS GASEOUS PHASE SENSORS

FIELD OF THE INVENTION

This invention pertains to gaseous analytes sensor devices comprising organic thin film transistor and, in particular, sensors able to perform the enantiomeric discrimination of gaseous analytes. Moreover the invention concerns with oligo (phenylenethienylenes) substituted with alcoxylic or alcoxylic chains functionalized with optically active amminoacids or monosaccharides, and their use for the construction of the abovementioned transistors.

DISCUSSION OF THE RELATED ART

The production of devices for volatile analytes recognition with sufficient reproducibility, stability, selectivity and low cost is still an open challenge for the analytical chemists and, the entire scientific community, has focused all the efforts on the ambitious project of developing devices able to simulate the behaviour of real "nose". Recently conducting polymer sensor arrays, addressed as "electronic noses", allow the identification and the classification of a broad spectrum of volatile organic compounds employing sophisticated computational methods for the pattern recognition of the responses. However, their performance level is still unable to fulfil the market requirements. For this reason organic systems capable of carrying out the volatile analytes recognition are currently studied with the aim of improving the organic thin film transistor sensor technology.

The great interest in sensor systems based on organic films originates from a series of potential benefits as: the possibility to taylor the chemical properties which allows the control of the selectivity for the analytes, the low (RT) operating temperature that allows the reduction of the power consumption, the miniaturization, as well as the lower production costs.

Generally speaking solid state devices with a resistor configuration have been employed.

More recently the attention has been directed towards the organic thin film transistor (OTFT) configurations which can be easily integrated into "on chip" device arrays for the recognition of the volatile analytes. These devices have shown very interesting responses with high repeatability and a output signal intensity depending on the gate bias. In addition OTFT based circuits for the analysis of volatile analytes have been already demonstrated.

For more than two decades the recognition of the analytes in the gaseous phase has been performed primarily using semiconductor gas sensors such as resistors, Schottky barrier, MIS capacitors, and MOSFET. Only later on, organic thin films have been employed as to active layer in gas sensors with the chemiresistor configuration, where the exposure of the organic films to the analyte causes the variation of the electrical resistance or of the conductibility of the films. Such variation is directly correlated to the gas concentration. On the other hand, the operational modalities of the OTFT gas sensors are quite different. As a matter of fact, the above mentioned devices operates as multiparametric sensors, thanks to the possibility of measuring simultaneously and at room temperature, four electrical parameters when the devices are directly exposed to the analyte vapours. The field effect mobility and the $I_{on}/I_{off}$ current ratio, as well as the threshold voltage and the bulk conductivity of the organic film, constitute the four output parameter used to characterize an OTFT as gas sensor. The first parameter is typical of the organic material used as active layer, while the others are representative of the device and can be easily extracted from the experimental data. The specification of an analyte can thus be accomplished by measuring in a "CHEMFET" set of parameters that can be considered as the finger print of the analyte.

Apart from being multiparametric devices, the field effect transistors (FET) with organic semiconductor as active layers, have the required reliability characteristics. In fact, the organic systems used as active layers in OTFT gas sensors generally form polycrystalline films with a high surface-to-volume ratio which amplifies the interaction of the films with the analyzed molecules.

One fundamental characteristic of the polymeric and oligomeric conductors is the effective modulation of the physical-chemical properties of the materials by the introduction of suitable substituentes whose sterical and electronics effect combined with their physical-chemical characteristics affect the general behaviour of the compounds. Therefore the use of such molecules for the construction of chemical sensor conjugates the electrical properties, typical of the inorganic semiconductor, with the ability of control the analyte interactions through the appropriate functional groups.

Poly and oligo(phenyleneethynylenes) are known to be used as organic semiconductors for OTFTs, as well as for LEDs, sensors and LC displays polarizers. The possible optical and electrical applications of these molecules are due to their easy processability and to the possibility of tuning the chemical structure of the unsaturated monomer.

Recently, copolymers bearing phenylene and thienylene moieties have attracted considerable interest in electronic and optoelectronic applications. In particular, poly(phenyleneth-ienylenes) substituted with different functional groups have been studied as materials for optoelectronics in order to develop light emitting polymers with high efficiency.

Detailed studies have demonstrated that thienyl and phenyl rings can be combined in a variety of molecular frameworks of semiconductor oligomers suitable as active layers in FET devices.

Alkoxy-substituted poly(phenylenethienylenes) have been also used as active layers in chemoresistive gas sensors for toxic gas detection, such as nitrogen dioxide ($NO_2$) sensing.

The fabrication of a new generation of gas sensors for chiral discrimination actually represents one of the most challenging goals in several fields of both academic and industrial research.

The problem of enantiomeric discrimination is particularly important in pharmaceutical industry. In fact, contrary to natural products, many synthetic chiral drugs are prepared and purchased as racemic mixtures. However, the high degree of stereoselectivity of many biological processes leads to consider that the two enantioners of a racemic mixture used as a drug are two entities with different efficacy.

One of the two enantiomers is often the active isomer, (eutomer) while the other one, (distomer) acts in a completely different way, thus being an antagonist or inducing collateral effects or sometimes toxicity; therefore, from a pharmaceutical point of view, the enantiomeric composition of chiral drugs is crucial because it affects the drug absorption, distribution, metabolism and elimination.

The importance of enantioselective analysis is growing also in fields, such as the food quality analysis: indeed many components of food are chiral and they are present as enantiomerically pure or in a definite enantiomeric ratio, by virtue of the homochiral nature of natural macromolecules. The enantioselective analysis allows, in this case, to evaluate the rise of fermentation or of ageing that alter the enatiomeric ratio and to detect if synthetic racemic ingredients have been added, thus offering a powerful tool against possible sophistication.

At present, gaschromatography (GC) is the technique mainly used for enantioselective analysis in the gas phase, even if it is a off-line technique The enantiomeric discrimination by sensing is, in principle, more difficult than GC methods but it occurs in real time, while chromatographica analysis require longer time. For instance, the GC analysis of D and L isomers of citronellol requires elution times longer than 66 minutes for each isomer and, furthermore, resolution is very low.

Moreover it must be necessarily used as a "off-line" analytical technique and it is not suitable for the growing demand of systems for analysis/control of "on-line" processes. Then, it is worthnoting that, in the case of some chiral molecules, such as the two enantiomers of β-citronellol, an efficient separation and discrimination cannot be attained via GC. GC analysis performed by chiral columns made of β-cyclodextrines (useful to well discriminate chiral alcohols, ketones, terpenes etc.) is often not useful for the two citronellols separation and, in the rare cases in which it is useful, separation occurs with resolution degree lower than 1, that is highly insufficient.

DESCRIPTION OF THE INVENTION

The task of this invention is to provide a organic thin film transistor useful as gas phase analyte sensor.

One aim of the present invention is to propose a new configuration of devices for the production of OTFT sensors.

Another aim of the present invention is to provide suitable compounds for the development of different configurations of active layers in transistors allowing both good conductive properties and enantioselective recognition of compounds in gas phase.

A particular target of the present invention is to propose a OTFT sensor showing enhanced sensitivity when it works at charge accumulation regime.

Then, another aim of the present invention is to provide a transistor with the above mentioned feature and also useful for efficient recognition of analytes in gas phase.

A further target of the present invention is to propose an efficient protocol for the fabrication of the above mentioned type of transistor.

According to a first aspect, the invention deals with new organic compounds with formula (I)

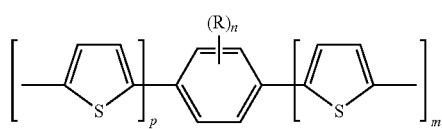

where
n is integer ranging from 1 to 4
m and p are equal or different and they are integer ranging from 0 to 5, as long as at least one of them is different from 0;
R is
an alkoxy chain $C_1$-$C_{12}$, eventually substituted with an optically active aminoacid, or
a monosaccharide moiety or its derivative;
and R groups are equal or different when n is different from 1

When m and/or p are integer ranging from 2 to 5, the thienyl groups are connected one another by the bond reported in the following formula, thus leading to 2-2'-bis-, tris-, tetra-o penta-thienyl chains

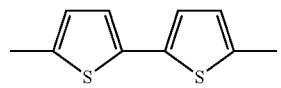

According to the present invention, the "alkoxy chain $C_1$-$C_{12}$" means a linear or branched saturated or unsaturated alkoxy chain with a number of carbon atoms ranging from 1 to 12.

According to a favourite aspect of the present invention, this alkoxy chain is saturated and linear.

According to a favourite aspect of the present invention, this alkoxy chain has a number of carbon atoms preferably ranging from 5 to 10 than from 6 to 9.

According to a particularly favourite aspect of the present invention, the alkoxy chain is functionalized with an optically active aminoacid or with a monosaccharide unit or a monosaccharide derivative unit and this alkoxy chain has 6 carbon atoms.

According to a favourite aspect of the present invention, the above mentioned aminoacid is selected among natural aminoacids, in the D or L form.

According to a favourite aspect of the present invention, this aminoacid is linked to the alkoxy chain by its amino or carboxy groups.

According to a favourite aspect of the present invention, the aminoacid is protected at the group that is not linked to the alkoxy chain by means of a appropriate conventional protective group.

According to a favourite aspect of the present invention, the above mentioned units of monosaccharide or of its derivatives consist in glucose, in case, bearing acetylated OH groups.

A fruitful protective group for amino group protection is the tert-butoxycarbonyl group (Boc).

According to another favourite aspect of the present invention, the alkoxy chain R is not functionalized with the aminoacid.

According to another favourite aspect of the present invention, n is different from 1 and R groups are equal.

Among compounds with formula (I), according to the present invention, the compounds of formula (I') are preferred

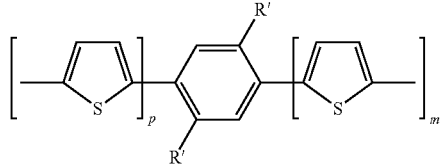

where
m e p are equal or different and are integer ranging from 0 to 5, as long as at least one of them is different from 0;
the R' groups are equal or different and they represent
a monosaccharide unit or a monosaccharide derivative unit, or a —O-Alk-R" group, in which
  Alk means a kinear alkyl chain $C_1$-$C_{12}$,
  R" means
    a hydrogen atom,
    a aminoacid substituent with formula (a)

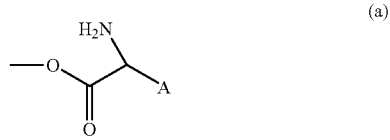
(a)

in which A means the remaining part of aminoacidic structure and $NH_2$ is, in case, protected, the aminoacid group (a) being in optically active form.

According to a favourite aspect of the present invention, the two groups R' are equal.

According to a favourite aspect of the invention, Alk means a linear alkyl chain with a number of carbons ranging from 5 to 10.

According to a favourite aspect of the invention, A completes a substituent selected between the D and L phenylalanine.

According to a favourite aspect of the invention, the Boc is the protective group.

According to a favourite aspect of the invention, n is 2.

According to a favourite aspect of the invention, both m and p are 2.

According to a favourite aspect of the invention, m e p are different and they can be 0, 2, 3 o 4 independently from one another.

When m and p is zero, the substituent R or R' can be attached at whatever position of phenyl ring in compounds with (I) e (I').

According to a favourite aspect of the invention, when in or p is zero, R or R' group is in para position to the thienyl group (or to the chain of thienyl groups).

The compounds particularly favoured according to the invention are selected among:
  1,4-bis[5-(2,2'-bithiophenyl)]2,5-bisoctyloxybenzene, herein also called PTO;
  6-{2,5-bis[2,2']bithiophen-5-yl-4-[6-(2S)-2-tert-butoxycarbonylamino-3-phenyl-propionyloxyi)hexyloxy] phenoxyl}hexyl ester of (2S)-2-tert-butoxycarbonylamino-3-phenylpropionic acid, herein also called PTA;
  1,4-bis[2,2']bithiophen-5-yl-2,5-bis-(2,3,4,6-tetra-O-acetyl-β-D-glucopiranosyl)benzene, herein also called PTZ;
  6-{4-[2,2']bithiophen-5-yl-phenoxy}hexyl ester of (2S)-2-tert-butoxycarbonylammino-3-phenylpropionic acid, herein also called DTA; and
  (2,2'-bithiophen-5-yl)-4-[2,3,4,6-tetra-O-acetyl-β-D-glucopiranosyl]benzene, herein also called DTZ.

According to the invention, compounds PTA, PTZ, DTA e DTZ are in optically active form, this meaning that they can be isomers in pure form, alternatively, they can represent a racemic mixture enriched of one of the two enantiomers.

Compound PTO can be prepared by a synthetic protocol shown in the following Scheme (I):

Scheme (I)

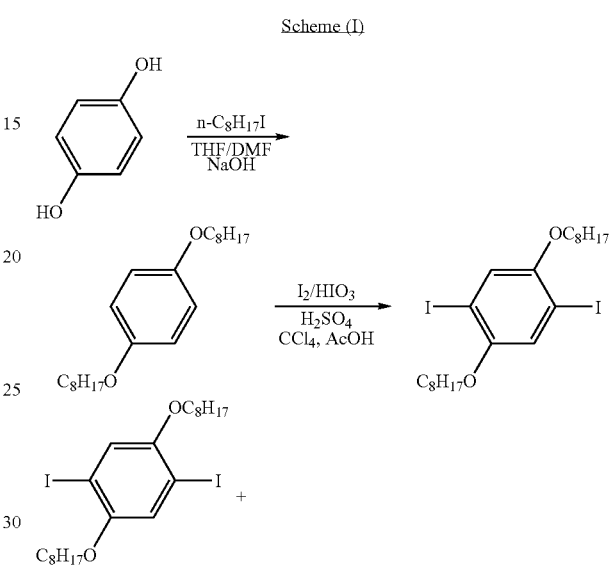

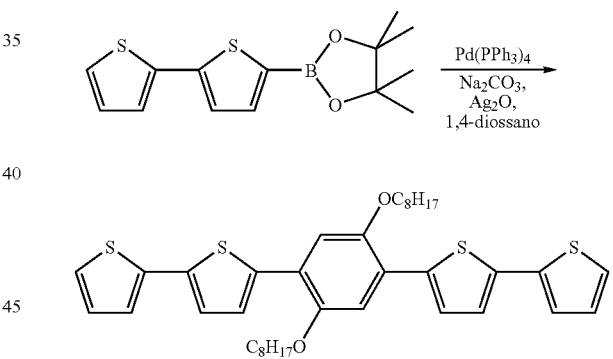

The other compounds with formula (I) bearing not substituted alkoxy groups R can be prepared using the same procedure.

Compound PTA can be synthesized by the synthetic protocol reported in the following scheme (II):

Scheme (II)

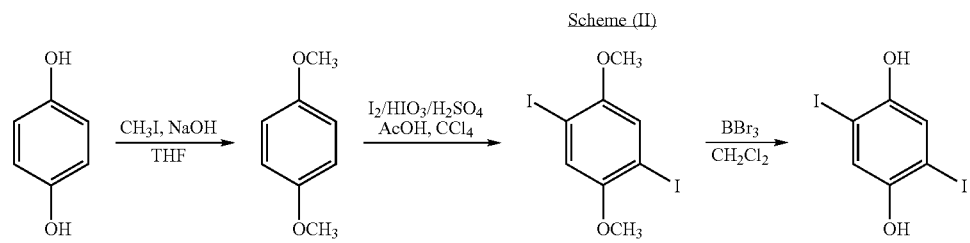

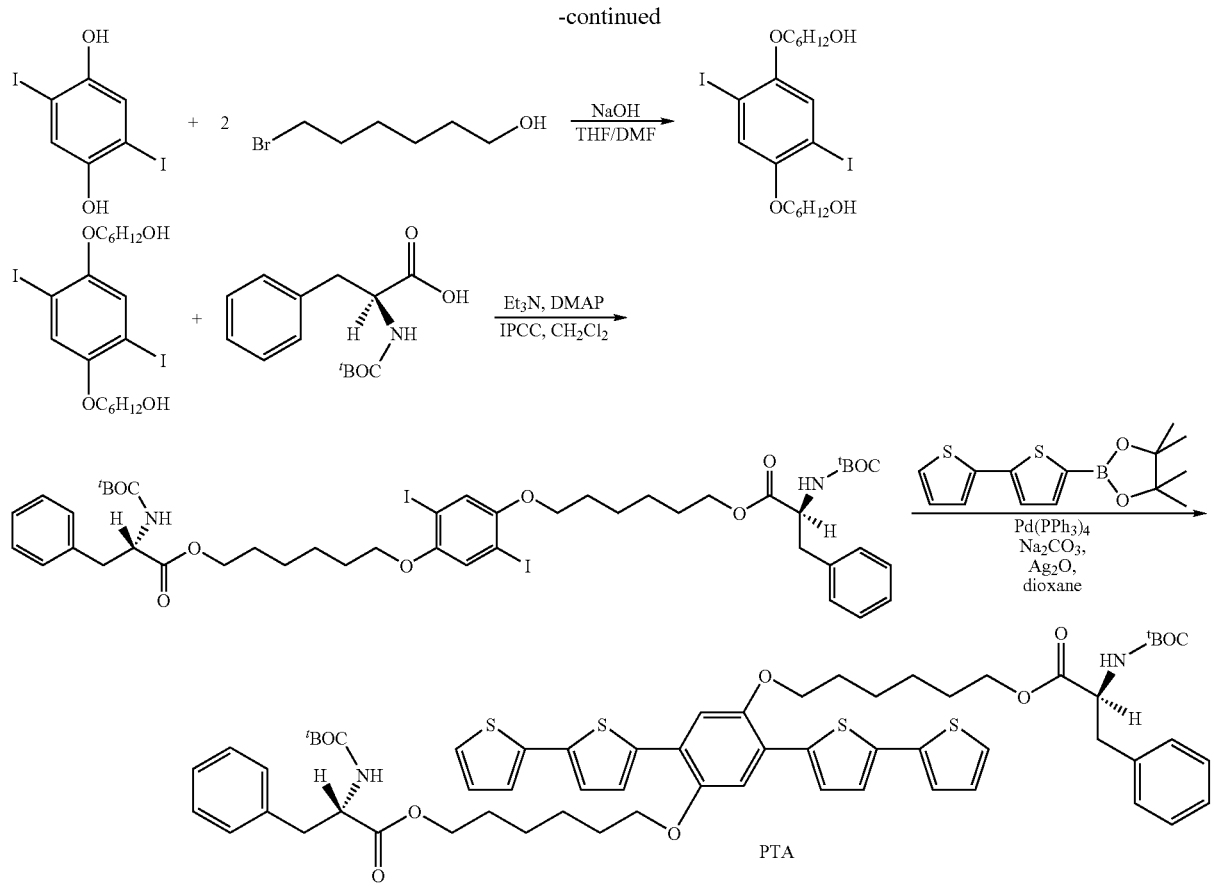
The other compounds with formula (I) in which R is an alkoxy group functionalized with an aminoacid can be prepared by the same protocol.
Compound PTZ can be obtained via the synthetic strategy shown in the following scheme (III).
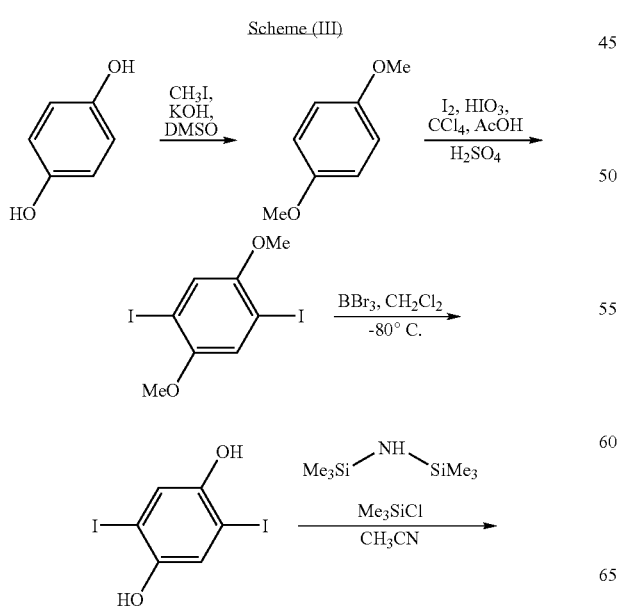
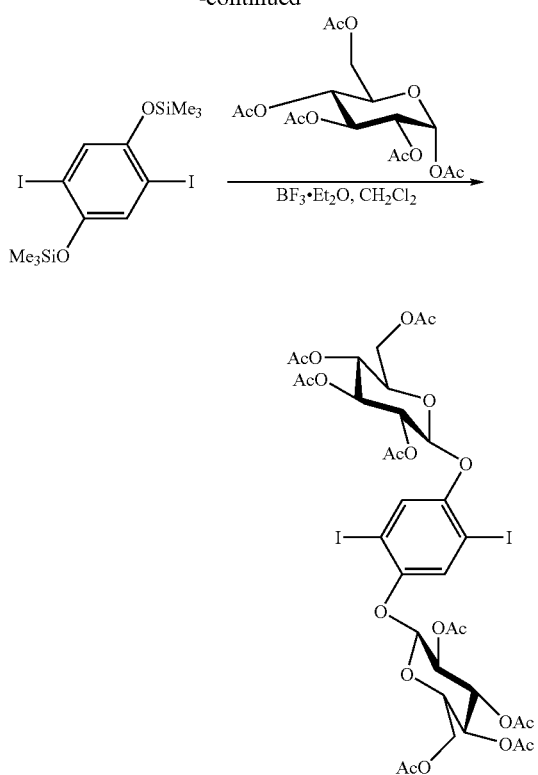

The synthesis of oligomer DTZ has been performed via the synthetic protocol reported in the scheme (IV).

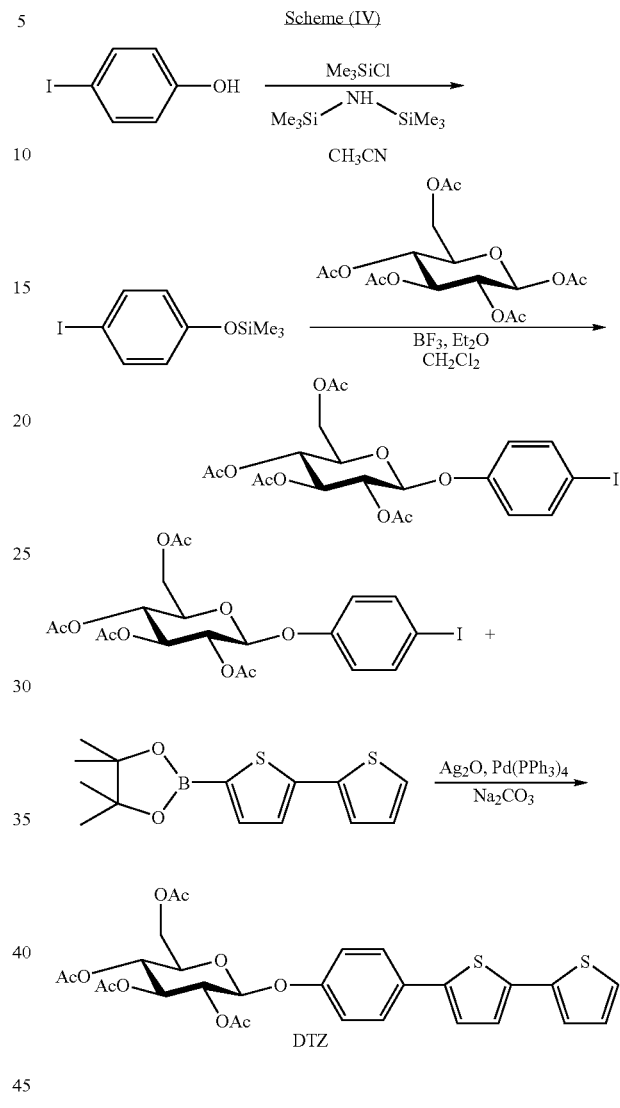

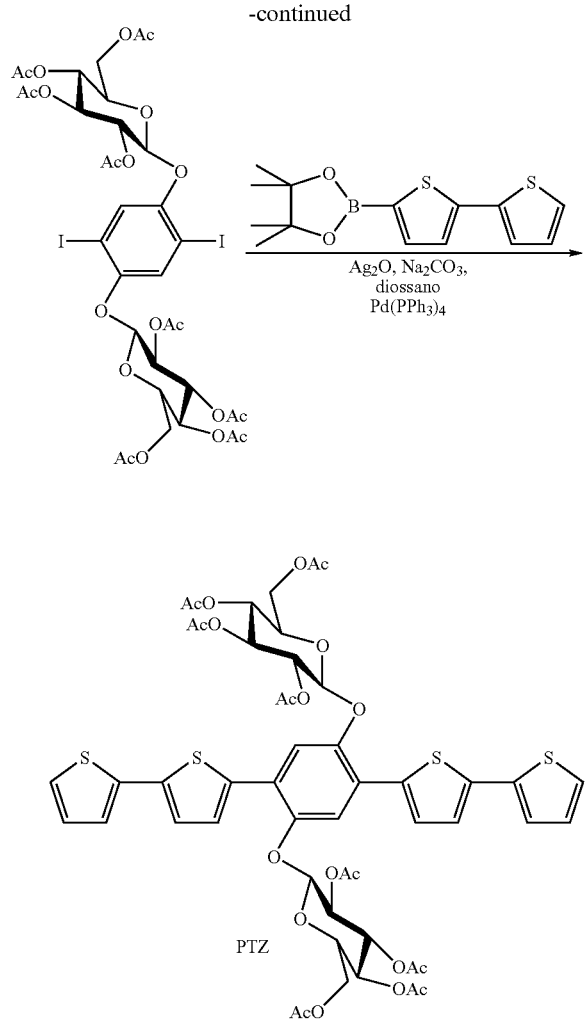

This synthetic scheme firstly involves hydroquinone alkylation performed in basic conditions. The following synthetic steps are iodination of dimethoxyhydroquinone using iodine/iodic acid and, then, demethylation with boron tribromide. The conversion of hydroquinone in its dimethylether is necessary because it is not possible to perform the direct iodination of hydroquinone. The introduction of two glucose units is carried out by glycosidation reaction of the bistrimetilsilyl ether of diiodoanthraquinone using boron trifluoride and glucose pentaacetate. Then, the Suzuki-Miyaura coupling reaction with the pinacol boronic ester of bithiophene leads to PTZ.

The other compounds with formula (I) in which R is a monosaccharide unit or a monosaccharide derivative unit can be synthesized by the same procedure.

DTZ is prepared by Suzuki-Miyaura coupling of the boronic ester of bithiophene with the product of glycosidation of p-iodophenol trimethylsilyl ether with glucose pentaacetate.

The other compounds with formula (I), in which R is a monosaccharide unit or a monosaccharide derivative unit and m or p is zero, can be synthesized by the same procedure.

Compound DTA is synthesized according to the protocol shown in the scheme (V):

Scheme (V)

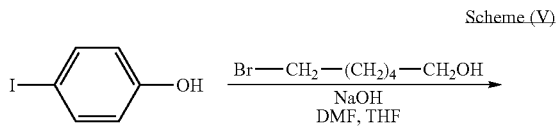

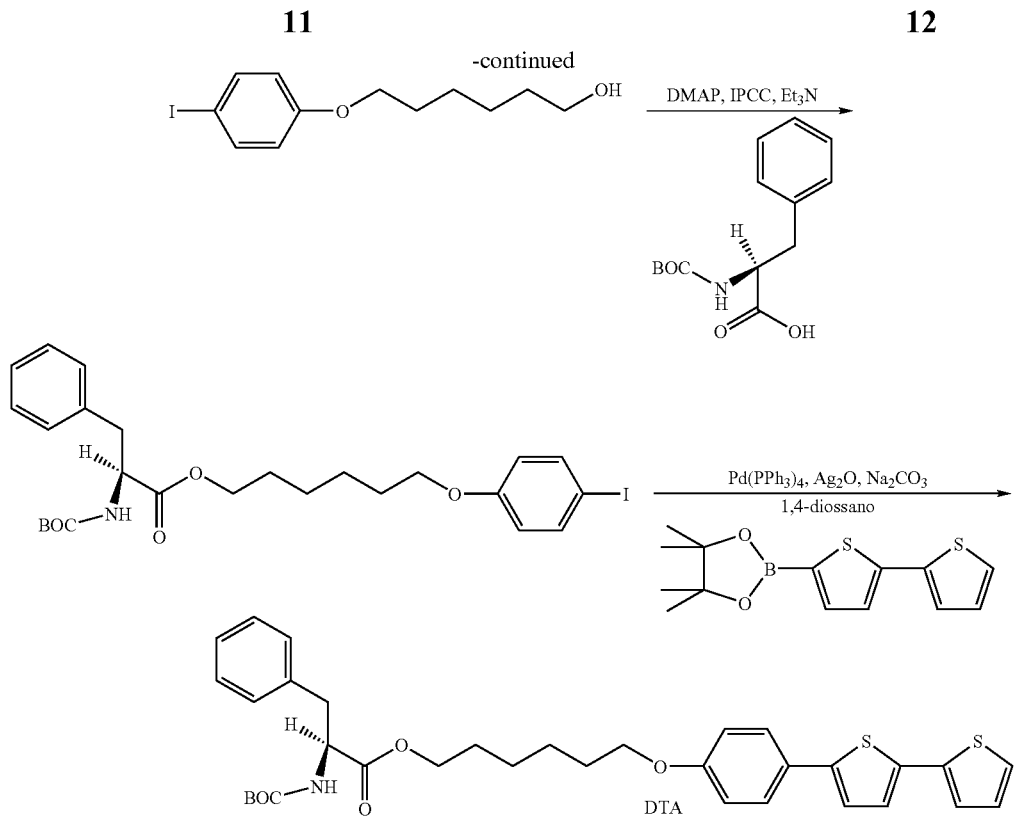

The first step involves the functionalization of the phenol hydroxy group with a six carbon alkoxy chain bearing a terminal hydroxy group. This terminal unit is, then, subjected to esterification with the carboxy group of the Boc-protected L-phenylalanine. The last step is based on a Suzuki-Miyaura cross-coupling process of the boronic ester of dithiophene with the aryl iododerivative functionalized with the aminoacid bearing spacer.

The other compounds with formula (I), in which R is a alkoxy group functionalized with aminoacid units and m or p is zero, can be synthesized by the same procedure.

Compounds with formula (I), advantageously the ones with formula (I') and more advantageously the compounds PTO, PTA, PTZ, DTA e DTZ can be used in the fabrication of active layers for transistors above described.

Therefore, according to another aspect, the invention deals with the application of one or more compounds with formula (I), suitably selected among compounds with formula (I'), in transistors for enantiomeric recognition of chiral molecules in gas phase.

Another aspect of the invention is the use of one—or more than one—compounds with formula (I) or—more advantageously—with formula (I') as active layer in a thin film transistor with a bilayer configuration.

The combination of the PTO, PTA, PTZ, DTA and DTZ for the construction of transistors to be used as gas sensor and for the recognition of enantiomeric compounds is the most appealing characteristic of the invention.

According to another aspect of this invention the transistor is constituted of at least one conducting layer, one dielectric layer and one semiconducting organic thin film. The last comprises one or more than one organic layers of compounds with formula (I) or more valuably with formula (I').

In the preferred form of the invention, the organic thin film of the transistor comprises at least two layers (bilayer) of different compounds.

In particular the organic thin film includes at least one layer of a compound with formula (I) bearing an unsubstituted alxoxydic chain or a compound with formula (I') wherein R" is a hydrogen atom, and at least one layer of a compound with formula (I) or (I') is in the optical active form.

A transistor according to the invention can have an organic thin film which includes from 5 to 30 overlapped Langmuir-Schäfer or LS transferred layers (since this is the preferred deposition technique) of a compound with formula (I) bearing an unsubstituted alcoxylic chain or a compound with formula (I') wherein R" is an hydrogen atom, and/or a compound with formula (I) or (I') in the optical active form.

The term "LS transfer" is used in this description for the identification of a single portion with a nanometric thickness, to be considered as a single molecular sheet of the active layer which is deposited on the dielectric layer until the desired active layer thickness is reached. With the term "layer" we identify each of the conducting and dielectric layers which constitute the transistor substrate, as well as each of the organic thin film active layers made of any of the compounds named as PTO, PTA, PTZ, DTA e DTZ. The term "bilayer" identifies an organic thin films formed by at least two different organic layers as in the case of PTO+PTA, PTO+PTZ, etc.

In the preferred form, the organic thin film includes 15 overlapped LS transferred layer of a compound with formula (I) bearing an unsubstituted alcoxylic chain or a compound with formula (I') wherein R" is an hydrogen atom, and/or a compound with formula (I) or (I') in the optical active form.

More preferably, a transistor with a recognition/selectivity properties comprises an organic thin film including 10 overlapped LS transferred layer of a compound with formula (I) bearing an unsubstituted alcoxylic chain or a compound with formula (I') wherein R" is an hydrogen atom like the PTO and 5 overlapped LS transferred layer of a compound with formula (I) or (I') in the optical active form like the compounds PTA, PTZ, DTA e DTZ.

A transistor according to this invention is preferably a field effect transistor (FET) wherein the gate electrode is directly in contact with the conducting layer.

These devices, employed as gas sensor for the recognition of volatile analytes, represent the solution to the problem of chiral discrimination of many substances of biological and environmental interest. In particular, the device sensitivity increases in the charge accumulation mode. Moreover, their main peculiarity is the easy integration on a chip in a matrix architecture (i.e. array) for the recognition and the classification of a broad spectrum of volatile organic compounds through the analysis of the responses by means of sophisticated "pattern recognition" computational methods, with the aim to simulate the molecular recognition ability of the mammalian olfactory system.

The abovementioned reasons justify the great interest of the present invention in the OTFT sensor field, considering especially both the huge financial and technological resources of the microelectronic industry, and in particular the plastic electronic industry which deals with the miniaturization and the integration of the organic transistors in integrated circuits.

According to another aspect of this invention a process for fabricating a semiconducing organic thin film transistor, which comprises the following steps, is proposed:
a) Preparation of at least one conducting layer;
b) Deposition on the conducting layer of at least one dielectric layer;
c) Deposition on the dielectric layer of at least one semiconducting organic thin film comprising one or more than one organic layers of compounds with formula (I) or with formula (I').

In particular according to the process proposed in this invention, the organic thin film is composed of two organic layers (bilayer) made of different compounds.

After the deposition of the dielectric material, a portion of the dielectric is removed in order to put in contact the gate electrode with the conducting layer.

Before the deposition of the organic thin film both the dielectric layer and the conducting layer are cleaned in order to remove the manufacturing residues.

In order to promote the deposition of the organic thin film an adhesion promoter can be usefully employed.

The deposition of the organic thin film can be thus accomplished by means of "drop casting", "spin coating thermal evaporation" deposition techniques as well as by means of Langmuir-Schäfer (LS) deposition techniques, the last as the most preferred.

After the deposition of the organic thin film the gold drain and source electrodes are fabricated on the organic semiconducting layer by thermal evaporation through a shadow mask.

DESCRIPTION OF THE DRAWINGS

Further aspects and advantage of this invention will be highlighted in the following description of figures, which is proposed for the sake of better illustrating, but not to limit: the figures include:

FIGS. 6A and 6B are diagrams of the characteristic curves obtained from organic thin film transistors fabricated with the preferred deposition technique employing the PTO to obtain a film comprising 5 LS transfer;

FIG. 7 is a diagram of a characteristic curve obtained from an organic thin film transistor transistors fabricated with the preferred deposition technique employing the PTO with pressure values different from those preferred;

FIGS. 13A and 13B illustrate some significant characteristic curves of the experimental evidence of the gaseous analytes detection, for the compounds at a first concentration level. These curves were obtained using an organic thin film transistor including an LS transferred layer of PTO;

FIGS. 13C and 13D illustrate some significant characteristic curves of the experimental evidence of the gaseous analytes detection, for the enantiomeric compounds at a second concentration level. These curves were obtained using an organic thin film transistor including an LS transferred layer of PTO;

In FIG. 1 an organic thin film transistor (OTFT) in the "bilayer" configuration is schematically depicted according one of the possible realization of the present invention. The transistor includes one conducting layer 10 and at least one dielectric layer 20 that together with the substrate 12 form a field effect transistor. The conducting layer can be made of silicon, p-type doped, while the dielectric layer can be made of silica ($SiO_2$).

Figure 1:
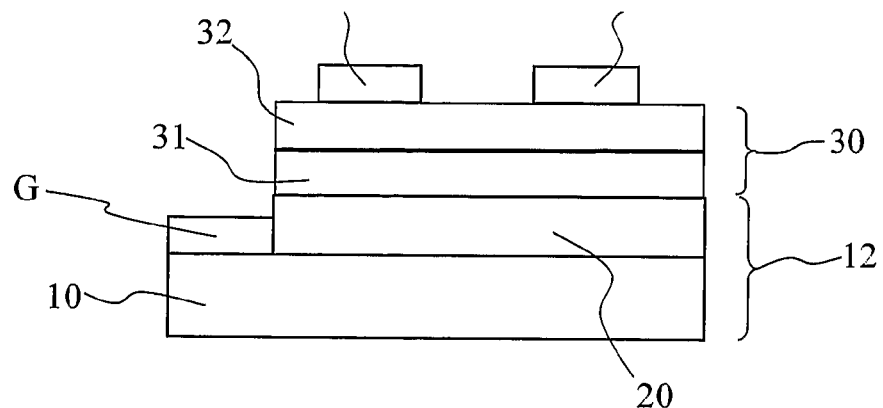
FIG. 1 is a schematic cross sectional view of an organic thin film transistor in a "bilayer" configuration according to one of the possible realization of the present invention.

On the dielectric layer the organic thin film 30 is deposited as semiconducting material, formed in this case by two different layer 31 and 32 made of different compounds. In particular, the organic thin film 30 comprises one layer 31 made of a compound with formula (I) bearing an unsubstituted alcoxylic chain or a compound with formula (I') wherein R" is an hydrogen atom (such as the PTO) deposited on the dielectric layer 20, and one layer 32 made of a compound in the optical active form (such as PTA, PTZ, DTA, DTZ) having the recognition/selectivity properties, and thus more exposed to the analyte.

Each layer 31 and 32 which compose the film 30 is obtained by means of the LS transfer of the abovementioned compounds with formula (I) or (I'), and in particular as LS transfer of the compound named as PTO for the layer 31, on which overlies the LS transfer of the compounds named as PTA, PTZ DTA, DTZ for the layer 32.

The best experimental results during the detection of the analytes in the gaseous phase, when no chiral discrimination is required, were obtained with a transistor wherein the organic thin film 30 is constituted of only the layer 31 fabricated with 15 single transfer of PTO, while for the enantiomeric discrimination experiments the best results were obtained with a "bilayer" type transistor wherein the organic thin film is constituted of 10 single LS transfer of PTO to form the layer 31 and 5 LS transfer of PTA or PTZ (or also DTA and DTZ) to form the layer 32.

The gate electrode G of the transistor is put in contact with the conducting layer 10 according to a "bottom gate" configuration, while the source electrode S and the drain electrode D are fabricated on the semiconducting layer 32 of the organic thin film 30 ("top contact" configuration) in order to obtain the typical channel of the field effect devices FET.

In the same manner it has been fabricated transistors with source and drain electrodes placed in contact with the conducting substrate 20 and at the same time built-in the layer 31 made of PTO ("bottom contact" configuration), but the devices in top contact configuration have shown the better experimental results.

The ability of an OTFT of working as a multiparametric sensor can be attributed to the two different charge transport working regimes: a bulk or tridimensional transport, which takes place when the device is in the off state (no gate potential is applied) and a bidimensional transport, which takes place in a very thin region at the interface between the organic semiconductor 30 and the dielectric 20, when the gate G and the drain D are properly polarized with respect to the grounded source S.

When no gate potential is applied, at a fixed source-drain potential, the transistor works like a chemiresistor and the measured variation of the source-drain current is caused by the conducibility of the organic film, induced by the interaction with the analyte, or induced by the permeation of the analyte in the active layer down to the dielectric gate layer.

Instead, with the application of a gate bias, a more consistent variation of the bidimensional source-drain current is measured, this current is confined in the internal region of the organic semiconductor. After the exposition of the active organic layer to the analyte, some typical device parameter like the threshold voltage $V_{th}$ and the field effect mobility change since both depend on respectively the volumetric density of the trapped charge in the semiconductor and the potential barrier between the grain boundaries due to the polycristalline nature of the film. The interaction of the gas with the film can originate trapping-detrappimg processes of the free charges and the consequent increase or decrease of the potential barrier between the grain boundaries.

Figure 2:
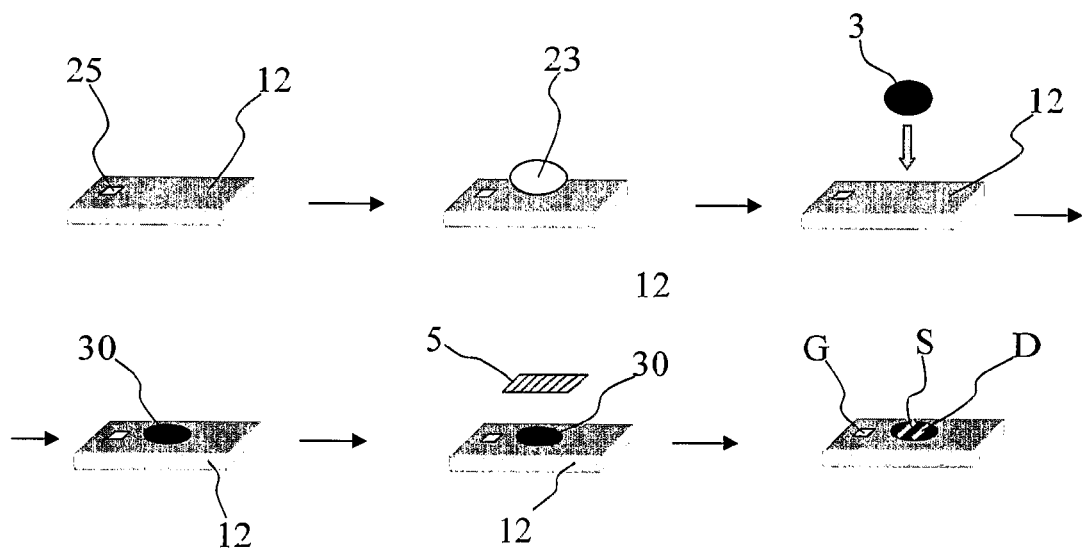
FIG. 2 illustrates a schematic representation of some of the step needed for the transistor construction according to the present invention.

In FIG. 2 are represented some of the step needed for the transistor construction according to the present invention.

Initially a substrate 12 formed by at least a silicon conducting layer 10 and at least a silica dielectric layer was prepared. A small portion of 25 of the dielectric layer was removed in order to fabricate successively the gate electrode After a suitable washing procedure for removing the manufacturing residues, the substrate 12 can be preventively treated with an adhesion promoter 23. The latter, depending on the employed deposition technique, could be useful for favouring a uniform distribution of the molecules on the substrate.

Then one or more LS transfers of a compound with formula I were carried out in order to form the transistor organic thin film 30. The deposition can be made according variuos known techniques, for instance by means of "drop casting", "spin coating thermal evaporation" or by means of Langmuir-Schäfer techniques.

After the deposition of the organic thin film preferably in a bilayer configuration and with the desired thickness composition characteristics, the gate G, source S and drain D electrodes can be fabricated by thermal evaporation of gold through a shadow mask 5. The final result is therefore a field effect transistor as that schematically represented in FIG. 1.

Concerning the compounds deposition for the obtainment of an organic thin film with the desired characteristics, the Langmuir-Schäfer deposition technique afforded the best results, in particular if preceded by the treatment of the substrate 12 with an adhesion promoter 23

The deposition according to the abovementioned techniques is performed keeping the compound 3 at a surface pressure included between 1 and 50 mN/m and preferably at a pressure matching with the condensed phase pressure of the compound.

The depositing was performed with a 5000 System 3 LB (850 $cm^2$) equipment. During the experiment, after each deposition, the vessel was accurately washed with chloroform, acetone, ethanol and water. As subphase high purity water (Millipore Milli-Q, 18.2 MØ cm) was used. The subphase temperature was setted at 20° C. by a Haake GH-D8 apparatus.

Both the functionalized compounds PTO and PTA were dissolved in $CHCl_3$ with a concentration of $2.50 \times 10^{-4}$ M. On the subphase was sprayed 200 μL of each solution by means of a gas tight syringe, adding small droplet of solution on different zone of the water surface. All the solvent, produced by Carlo Erba, were of spectrophotometric grade.

After the solvent evaporation, the floating film at the air-water interface was slowly and continuously compressed at 10 Å² rate for each repetition at minute. The surface pressure was contemporaneously monitored by a Wilhelmy balance while an isotherm curve of each sample was obtained.

Figure 3:
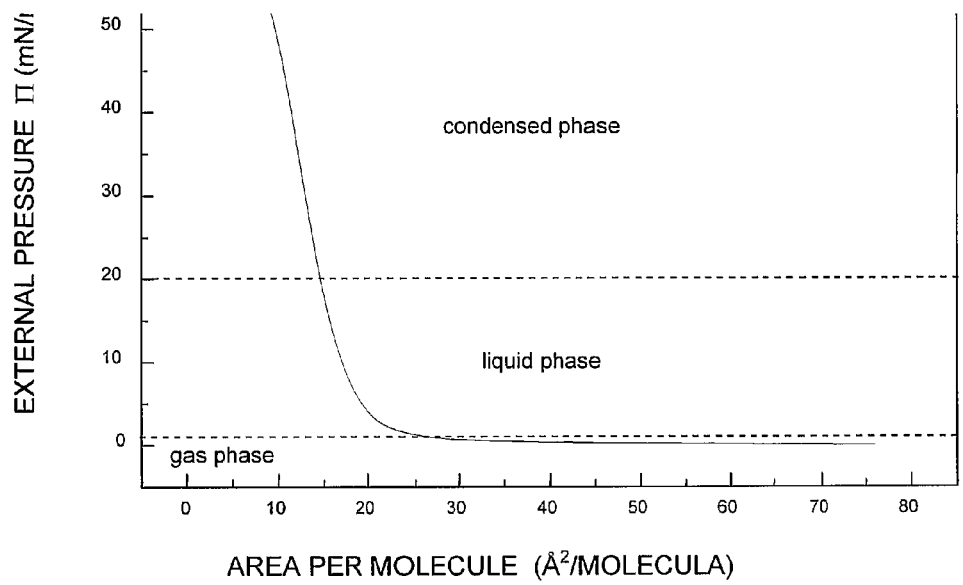
FIG. 3 is a diagram of the Langmuir isotherm of a compound reported in the present invention.

The molecular layer at the air-water interface was transferred by the Langmuir-Schäfer (LS) deposition technique, by lowering the substrate, holded in an horizontal position, until the contact with the floating film was achieved. During the transfer, a surface pressure of 20 mN/m for both functionalized compound was normally used. Before the transfer the substrates were hydrophobized by exposition for 24 hour to an 1,1,1,3,3,3-Hexamethyldisilazane saturated atmosphere used as received from Sigma-Aldrich In FIG. 3 is represented as an example the Langmuir isotherm curve for the PTO, as is evident form the figure the condensed phase for this compound is reached at surface pressure starting from 20 mN/m. This surface pressure value was the best for the fabrication of an organic thin film transistor with the desired performances.

Some experimental results are illustrated referring to the following example

Example 1

Synthesis of 1,4-bis[5-(2,2'-bithienyl)]-2,5-bis(octyloxy)benzene (PTO)

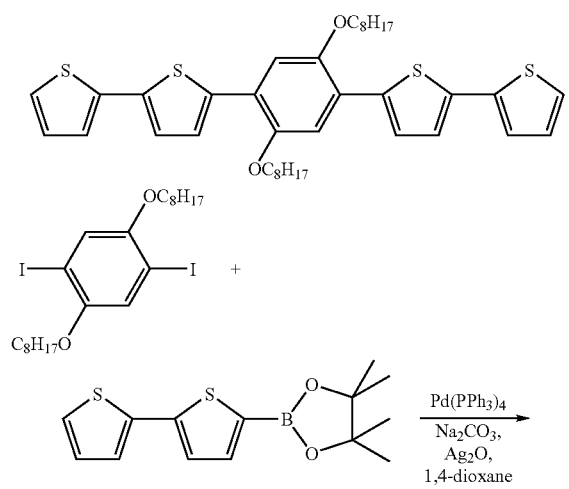

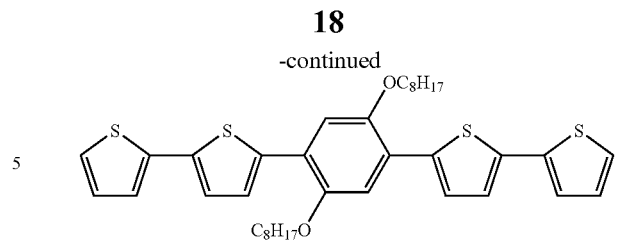

$Na_2CO_3$ (0.36 g 3.40 mmol), $Ag_2O$ (0.79 g 3.41 mmol) and $Pd(PPh_3)_4$ (0.06 g 0.052 mmol) were added to a stirred solution of 5-(4,4,5,5-tetramethyl-1,3,2-dioxaborolan-2-yl)-2,2'-bithiophene 2 (1.10 g, 3.76 mmol) and 1,4-diiodo-2,5-dioctyloxybenzene (prepared as reported in the literature: Bao, Z.; Chen, Y.; Cai, R.; Yu, L. *Macromolecules* 1993, 26, 5281) (1.00 g, 1.71 mmol) in 20 ml of dry 1,4-dioxane kept under nitrogen atmosphere. The reaction mixture was warmed up to the reflux temperature. After 8 hours refluxing, the reaction mixture was cooled to room temperature, and the solvent was then evaporated at reduced pressure. An aqueous saturated solution of $NH_4^+Cr^-$ was then added, and the mixture was extracted with ethyl acetate. The organic extracts were dried with anhydrous sodium sulphate, filtered and the solvent was evaporated at reduced pressure. The residue was percolated on a celite column and the crude product was purified by column chromatography over silica gel, using a mixture of petroleum ether and dichloromethane (8:2) as the eluent. A yellow solid was obtained, which was further purified by crystallization from dichloromethane-hexane (0.99 g, 88% yield), (m.p.: 149-151° C.), and characterized on the basis of the following NMR spectral data:

¹H NMR (500 MHz, $CDCl_3$): δ 0.89 (t J=6.7 Hz, 6H) 1.24÷1.45 (m, 16H), 1.58 (quintet, J=6.4 Hz, 4H), 1.94 (quintet, J=6.4 Hz, 4H), 4.12 (t, J=6.4 Hz, 4H), 7.04 (tl, J~4 Hz, 2H), 7.17 (d, J=3.9 Hz, 2H), 7.20÷7.25 (m, 4H), 7.24 (s, 2H), 7.47 (d, J=3.9 Hz, 2H) ppm.

¹³C NMR (125.7 MHz, $CDCl_3$), δ 14.12, 22.68, 26.36, 29.30, 29.43, 31.85, 69.73, 111.87, 122.62, 123.26, 123.48, 124.15, 125.75, 127.81, 137.25, 137.75, 138.09, 149.20 ppm.

Anal. Calcd. for $C_{38}H_{46}O_2S_4$: C, 68.84; H, 6.99; S, 19.34. found C, 68.58; H, 6.80; S, 19.21.

Example 2

Synthesis of 6-{2,5-bis-[2,2']bithiophen-5-yl-4-[6-(2S)-2-tert-butoxycarbonylamino-3-phenylpropionyloxy)hexyloxy]phenoxy}hexyl ester of the acid (2S)-2-tert-Butoxycarbonylamino-3-phenylpropionic acid (PTA)

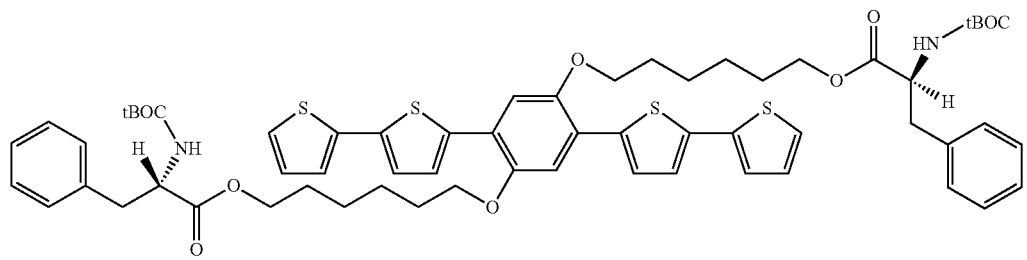

Example 2.1

6-[4-(6-Hydroxyhexyloxy)-2,5-diiodophenoxy]hexan-1-ol

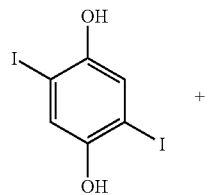

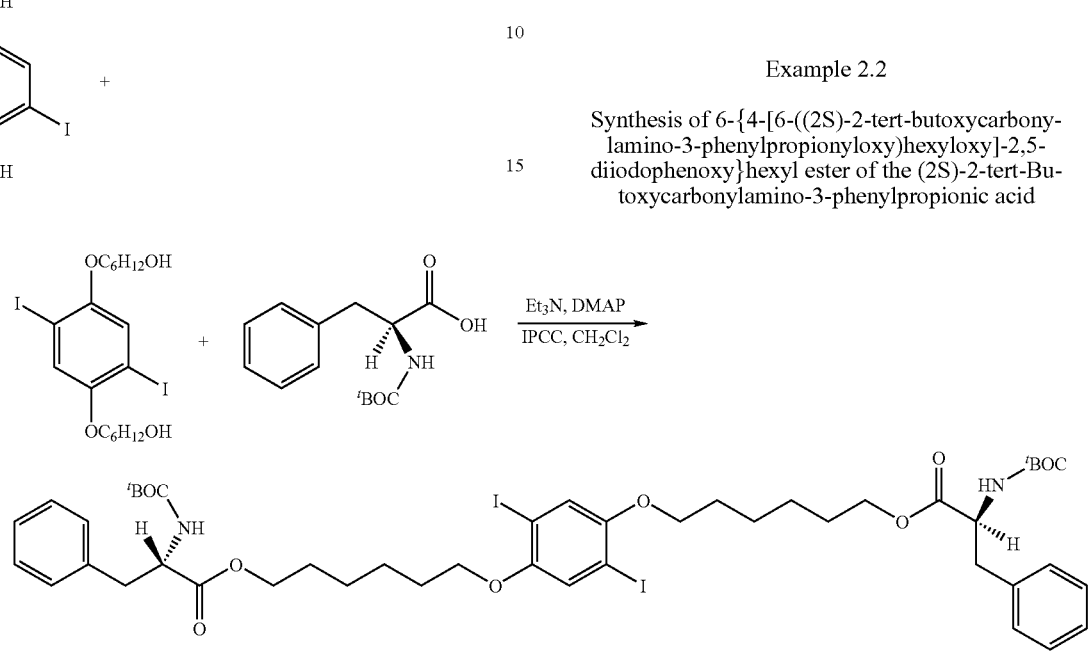

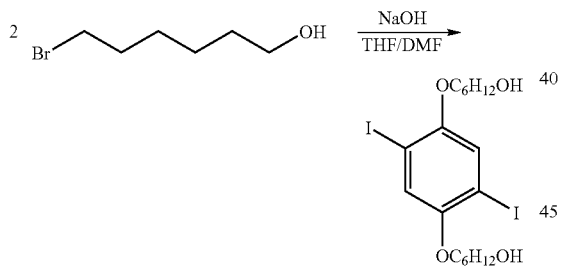

A solution of 2,5-diiodohydroquinone (1.80 g, 4.97 mmol) and NaOH (0.44 g, 11.00 mmol) in 2 ml of THF and 4 ml of DMF was stirred under $N_2$ atmosphere. After 20 minutes 6-bromo-1-hexanol (2.93 g, 16.10 mmol) was added dropwise, then the system was heated to 50° C.

After 48 h the reaction was quenched by adding an aqueous saturated solution of $NH_4Cl$. The product was extracted with dichloromethane. The organic phases were washed several times with a solution of NaOH (10%) and water to eliminate unreacted reagents and DMF, then dried over anhydrous $Na_2SO_4$. The solvent was evaporated at reduced pressure. The crude product was washed with diethyl ether and the solid purified by means of a short column of silica gel using dichloromethane/petroleum ether (7:3) to elute byproducts and then ethyl acetate to elute 1.49 g (53% yield) of a white solid.

IR (KBr): ν 3401, 3293, 2938, 2902, 2863, 1626, 1487, 1464, 1392, 1351, 1215, 1058, 1024 cm$^{-1}$; $^1$H NMR (500 MHz, CDCl$_3$): δ 1.35 (bs, 2H), 1.40÷1.49 (m, 4H), 1.51÷1.58 (m, 4H), 1.59÷1.66 (m, 4H), 1.78÷1.85 (m, 4H), 3.66 (t, 4H, J=6.7 Hz), 3.93 (t, 4H, J=6.3 Hz), 7.16 (s, 2H) ppm;

$^{13}$C NMR (125.7 MHz, CDCl$_3$): δ 25.31, 25.77, 28.97, 32.44, 62.51, 70.07, 86.23, 122.66, 152.66 ppm.

Anal. Calcd. for $C_{18}H_{28}I_2O_4$: C, 38.45; H, 5.02. Found: C, 38.24; H, 4.98.

Example 2.2

Synthesis of 6-{4-[6-((2S)-2-tert-butoxycarbonylamino-3-phenylpropionyloxy)hexyloxy]-2,5-diiodophenoxy}hexyl ester of the (2S)-2-tert-Butoxycarbonylamino-3-phenylpropionic acid Triethylamine (0.33 g, 3.26 mmol) and DMAP (0.072 g, 0.59 mmol) were added to a solution of N-BOC-L-phenylalanine (0.79 g, 2.98 mmol) and 6-[4-(6-Hydroxyhexyloxy)-2,5-diiodophenoxy]hexan-1-ol (0.75 g, 1.33 mmol) in 10 ml of dichloromethane. The mixture was cooled to 0° C. and isopropenyl chlorocarbonate (IPCC) (0.42 g, 3.49 mmol) was added dropwise under stirring for 10 min. After 60 min, ethyl acetate was added, and the organic phases were washed with an aqueous solution of potassium hydrogenosulfate (5%, 2×10 ml), then an aqueous solution of sodium hydrogenocarbonate (5%, 2×10 ml), and brine. The organic phases were dried over anhydrous $Na_2SO_4$ and the solvent evaporated at reduced pressure. The crude product was purified by chromatography on silica gel using petroleum ether/dichloromethane/ethyl acetate (8:2:2) as eluent obtaining 1.05 g (75% yield) of a dense yellow oil.

IR (KBr): ν 3438, 3025, 2938, 2864, 1713, 1493, 1459, 1350, 1211, 1168, 1055, 756 cm$^{-1}$;

$^1$H NMR (500 MHz, CDCl$_3$): δ 1.32÷1.40 (m, 4H), 1.42 (s, 18H), 1.48÷1.56 (m, 4H), 1.59÷1.67 (m, 4H), 1.75÷1.83 (m, 4H), 3.02÷3.20 (m, 4H), 3.92 (t, 4H, J=6.4 Hz), 4.04÷4.16 (m, 4H), 4.54÷4.62 (bm, 2H), 4.98 (bd, 2H, J~8 Hz), 7.13 (d like, 4H, J~7 Hz), 7.17 (s, 2H), 7.23 (t like, 2H, J~7 Hz), 7.28 (t like, 4H, J~7 Hz) ppm;

$^{13}$C NMR (125.7 MHz, CDCl$_3$): δ 25.14, 25.35, 27.98, 28.06, 28.59, 38.03, 54.21, 64.87, 69.61, 79.28, 85.97, 122.31, 126.56, 128.11, 128.95, 135.84, 152.42, 154.71, 171.60 ppm.

Anal. Calcd. $C_{46}H_{62}I_2N_2O_{10}$: C, 52.28; H, 5.91; N, 2.65. Found: C, 52.53; H, 6.22; N, 2.65.

Example 2.3

Synthesis of 6-{2,5-bis-[2,2']bithiophen-5-yl-4-[6-((2S)-2-tert-butoxycarbonylamino-3-phenylpropionyloxy)hexyloxy]phenoxy}hexyl ester of the (2S)-2-tert-Butoxycarbonylamino-3-phenylpropionic acid (PTA)

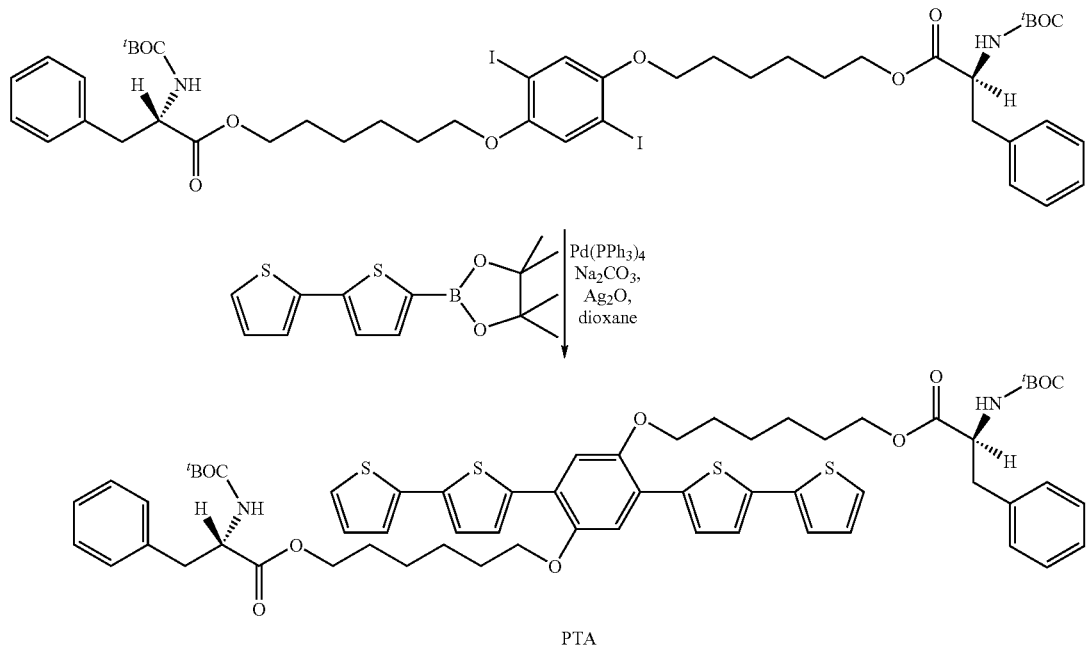

Anhydrous $Na_2CO_3$ (0.066 g, 0.623 mmol), $Ag_2O$ (0.144 g, 0.621 mmol) and $Pd(PPh_3)_4$ (0.011 g, 0.009 mmol) were added to a stirred solution of 5-(4,4,5,5-tetramethyl-1,3,2-dioxaborolan-2-yl)-2,2'-bithiophene (0.198 g, 0.678 mmol) and (2S)-2-tert-Butoxycarbonylamino-3-phenylpropionic acid 6-{4-[6-(2S)-2-tert-butoxycarbonylamino-3-phenylpropionyloxy)hexyloxy]-2,5-diiodophenoxy}hexyl ester (0.326 g, 0.308 mmol) in 5 ml of dry 1,4-dioxane kept under nitrogen atmosphere. The reaction mixture was refluxed overnight. Then, the mixture was cooled to room temperature, and the solvent was finally evaporated at reduced pressure. An aqueous saturated solution of $NH_4^+Cl^-$ (10 ml) was then added, and the mixture was extracted with dichloromethane (15 ml, three times). The organic extracts were dried with anhydrous sodium sulphate, filtered and the solvent was evaporated at reduced pressure. The crude product was purified by column chromatography over silica gel, using a mixture of petroleum ether/dichloromethane/ethyl acetate/(8:2:2) as eluent. A yellow solid was isolated (0.210 g, 60% yield), which was further purified by crystallization from hexane-dichloromethane (m.p. 121-123° C.).

The structure of the compound was proven by $^{13}C$ and $^1H$ NMR:

$^{13}C$ NMR (125.7 MHz, $CDCl_3$): δ 25.66, 25.96, 28.26, 28.29, 28.45, 29.25, 38.44, 54.44, 65.32, 69.51, 79.81, 112.05, 122.73, 123.31, 123.50, 124.27, 125.84, 126.94, 127.86, 128.47, 129.28, 136.04, 137.33, 137.64, 137.96, 149.19, 155.03, 171.96 ppm.

$^1H$ NMR (500 MHz, $CDCl_3$): δ 1.34÷1.48 (m, 4H), 1.42 (s, 18H), 1.61 (quintet, J=7.8 Hz, 4H), 1.63 (quintet, J=7.8 Hz, 4H), 1.93 (quintet 7.8 Hz, 4H), 3.01÷3.14 (m, 4H), 4.07÷4.17 (m, 8H), 4.53÷4.62 (bm, 2H), 4.99 (bd, J~8 Hz, 2H), 7.04 (dd, J=3.9, 5.1 Hz, 2H), 7.13 (dl, J~7.0 Hz, 4H), 7.18 (d, J=3.9 Hz, 2H), 7.19÷7.31 (m, 12H), 7.46 (d, J=3.9 Hz, 2H) ppm.

Anal. Calcd. $C_{62}H_{72}N_2O_{10}S_4$: C, 65.70; H, 6.40; N, 2.47; S, 11.32. Found: C, 65.63; H, 6.36; N, 2.51; S, 11.40.

Example 3

Synthesis of 1,4-bis[5-(2,2'-bithienyl)]-2,5-(2,3,4,6-tetra-O-acetyl-β-D-glucopyranosyl)-benzene (PTZ)

Example 3.1

Synthesis of 1,4-dimethoxybenzene

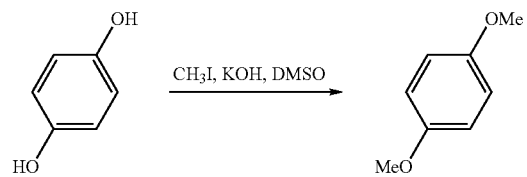 [SMILES: Oc1ccc(O)cc1 ; COc1ccc(OC)cc1]

Iodomethane (4.98 ml, 9.99 mmol) was added dropwise to a solution of hydroquinone (4.00 g, 36.33 mmol) and KOH (8.32 g, 148.30 mmol) in 75 ml of DMSO.

The reaction mixture became dark and was stirred at r.t. for 1 h at 25° C. The reaction mixture was neutralized by adding an aqueous saturated solution of $NH_4Cl$. The product was extracted with dichloromethane (3×50 mL). The organic phases were washed several times with water (5×150 mL) to eliminate DMSO, then dried over anhydrous Na$_2$SO$_4$. The solvent was evaporated at reduced pressure. A white solid was isolated (4.87 g, yield 97%).

Example 3.2

Synthesis of 2,5-diiodo-1,4-dimethoxybenzene

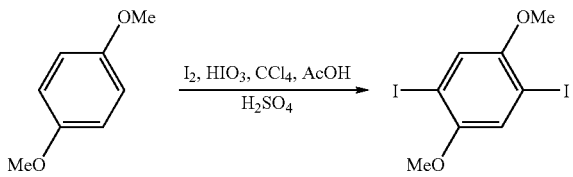 [SMILES: COc1ccc(OC)cc1 ; "H2SO4" ; COc1cc(I)c(OC)cc1I]

The reaction mixture, 1,4-dimethoxybenzene (5.00 g, 36.19 mmol), iodine (8.27 g, 32.58 mmol), HIO$_3$ (3.90 g, 22.17 mmol), H$_2$SO$_4$ (30%) (11.7 ml), acetic acid (63.3 ml), in 15 ml of Tetrachloromethane was refluxed for 12 hours. Then, the mixture was cooled to room temperature, the solvent was concentrated at reduced pressure and the crude product was collected by filtration and washed with acetone. A white solid was isolated (10.02 g, yield 71%).

Example 3.3

Synthesis of 2,5-diiodo-1,4-hydroquinone

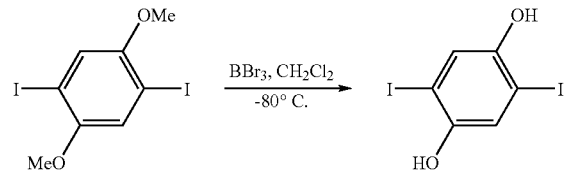 [SMILES: COc1cc(I)c(OC)cc1I ; "-80° C." ; Oc1cc(I)c(O)cc1I]

A solution of 2,5-diiodo-1,4-dimethoxybenzene (3.00 g, 7.69 mmol) in 30 ml of Anhydrous dichloromethane was cooled to −80° C. and BBr$_3$ (19 ml, 16.93 mmol) was added drop wise. The mixture was allowed to rt and stirred for additional 12 h, solid precipitate was formed, collected and then crystallized from ethanol-water. The trace of solvent was evaporated at reduced pressure (2.50 g, yield 90%).

Example 3.4

Synthesis of 1,4-bis-O-trimethylsilyl-2,5-diiodohydroquinone

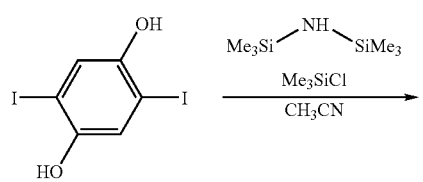

-continued

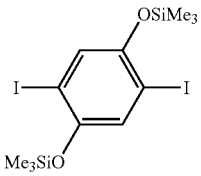

2,5-diiodo-1,4-hydroquinone (1.000 g, 2.76 mmol), chlorotrimethylsilane (0.77 ml, 6.07 mmol) and 1,1,1,3,3,3-hexamethyldisilazane (1.29 ml, 6.07 mmol) were dissolved in 6 ml of dry acetonitrile. The reaction mixture was stirred under nitrogen at r.t. for 16 h, and then the solvent was removed at reduced pressure. The residue was dissolved in petroleum ether and filtered to remove precipitated salts. The solution was washed with saturated aqueous bicarbonate and brine, dried over anhydrous Na$_2$SO$_4$, and evaporated to dryness. 1.308 g (94% yield) of the crude product were obtained.

IR (KBr): ν 2959, 1461, 1347, 1252, 1204, 1046, 908, 841 cm$^{-1}$;

$^1$H NMR (500 MHz, CDCl$_3$): δ 0.35 (s, 18H), 7.15 (s, 2H) ppm.

Example 3.5

Synthesis of 2,5-diiodo-1,4-bis-(2,3,4,6-tetra-O-acetyl-β-D-glucopyranosyl)benzene

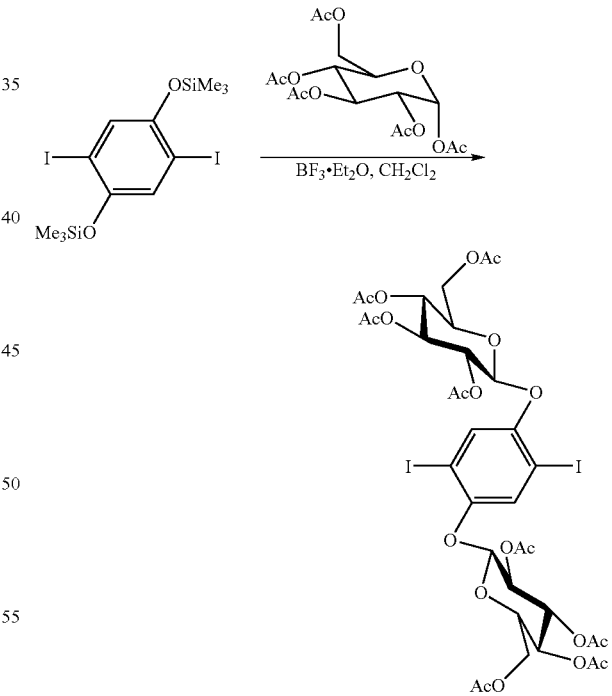

Glucose pentaacetate (2.100 g, 5.38 mmol), dissolved in 15 ml of dry dichloromethane, and BF$_3$.Et$_2$O (4.9 ml) were added to a solution of 1,4-bis-O-trimethylsilyl-2,5-diiodohydroquinone (1.240 g, 2.45 mmol) in 20 ml of CH$_2$Cl$_2$ under nitrogen atmosphere and at r.t. After 16 h the reaction mixture was washed with saturated aqueous bicarbonate and water, and dried over anhydrous Na$_2$SO$_4$. After evaporation of the solvent at reduced pressure, the crude product was purified by crystallization from methanol obtaining 1.477 g (59% yield) of a white solid (m.p.: 183÷185° C.).

IR (KBr): ν 2951, 1752, 1470, 1375, 1224, 1041, 904, 811, 603 cm$^{-1}$;

$^1$H NMR (500 MHz, CDCl$_3$): δ 2.04 (s, 6H), 2.05 (s, 6H), 2.09 (s, 6H), 2.16 (s, 6H), 3.89÷3.93 (m, 2H), 4.21 (dd, 2H, J=12.3, 6.0), 4.24 (dd, 2H, J=2.9, 12.3), 4.96 (d, 2H, J=8.0), 5.12 (tl, 2H, J=9.3), 5.25÷5.36 (m, 4H), 7.45 (s, 2H) ppm; $^{13}$C NMR (125.7 MHz, CDCl$_3$): δ 20.58, 21.07, 21.14, 62.18, 68.22, 70.66, 72.38, 72.47, 86.61, 100.02, 126.38, 152.65, 169.09, 169.38, 170.20, 170.64 ppm;

elemental analysis (%) calcd for $C_{34}H_{40}I_2O_{20}$: C, 39.94; H, 3.94. found: C, 39.83; H, 3.85.

Example 3.6

Synthesis of 1,4-bis[5-(2,2'-bithienyl)]-2,5-(2,3,4,6-tetra-O-acetyl-β-D-glucopyranosyl)-benzene (PTZ)

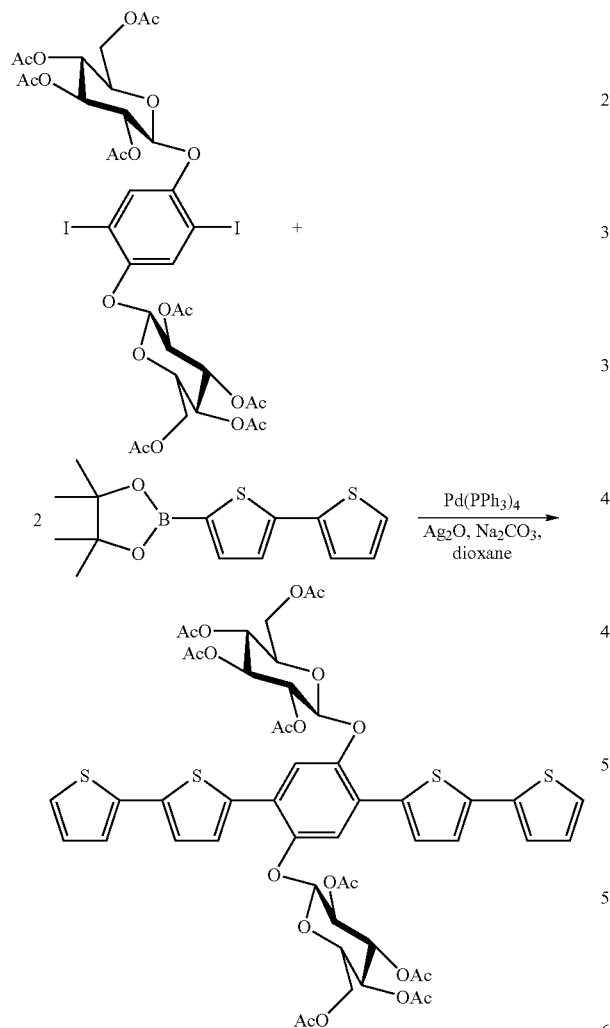

Na$_2$CO$_3$ (0.21 g, 1.98 mmol), Ag$_2$O (0.45 g, 1.94 mmol) and Pd(PPh$_3$)$_4$ (0.03 g, 0.03 mmol) were added to a solution of 1,4-bis-(2,3,4,6-tetra-O-acetyl-β-D-glucopyranosyl)-2,5-diiodobenzene (1.00 g, 0.98 mmol) and 5-(4,4,5,5-tetramethyl-1,3,2-dioxaborolan-2-yl)-2,2'-bithiophene (0.63 g, 2.16 mmol) in 30 ml of anhydrous dioxane under a nitrogen atmosphere. The reaction mixture was refluxed for 24 hours, and then the solvent was removed at reduced pressure. A saturated solution of NH$_4^+$Cl$^-$ (20 ml) was then added and the resulting mixture was extracted with ethyl acetate (3×15 ml). Organic extracts were dried over anhydrous sodium sulfate, the filtered and the solvent was finally removed at reduced pressure. The residue was percolated on a celite column and the crude product was purified by column chromatography over silica gel, using a mixture of petroleum ether/ethyl acetate 1:1 as the eluent, and then crystallized from dichloromethane-hexane. 0.90 (84% yield) of a bright yellow solid were recovered (m.p. 218-220° C.), which was identified on the basis of the following spectral data:

$^1$H NMR (500 MHz, CDCl$_3$), δ (ppm) 1.82 (s, 3H), 1.98 (s, 3H), 2.02 (s, 3H), 2.06 (s, 3H), 3.97-4.03 (m, 1H), 4.21-0.30 (m, 2H), 5.18 (t, 2H, J=9.5 Hz), 5.19 (d, 1H, J=8.3 Hz) 5.30 (t, 1H, J=9.5 Hz), 5.43 (dd, 1H, J=9.5, 8.3 Hz), 7.05 (dd, 1H, J=5.1, 3.5 Hz), 7.14 (d, 1H, J=4.0 Hz), 7.24 (dd, 1H, J=5.1, 1.0 Hz), 7.27 (dd, 1H, J=3.5, 1.0 Hz), 7.32 (d, 1H, 4.0 Hz), 7.43 (s, 1H).

$^{13}$C NMR (500 MHz, CDCl$_3$), δ (ppm) 20.39, 20.57, 62.29, 68.26, 70.91, 72.38, 72.99, 99.85, 115.50, 123.95, 124.67, 127.52, 128.07, 136.33, 136.92, 138.22, 148.84, 169.35, 169.45, 170.24, 170.65.

UV: λ$_{max}$ 394.50 nm, λ$_{min}$ 252.00 nm;

Example 4

Synthesis of (2,2'-bithiophen-5-yl)-4-[2,3,4,6-tetra-O-acetyl-β-D-glucopyranosyl]benzene (DTZ)

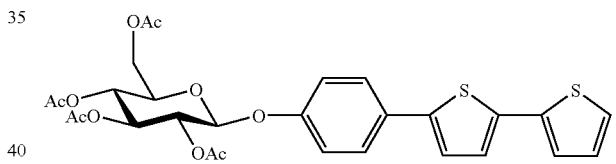

Example 4.1

Synthesis of 1-iodo-4(2,3,4,6-tetra-O-acetyl-β-D-glucopyranosyl)benzene

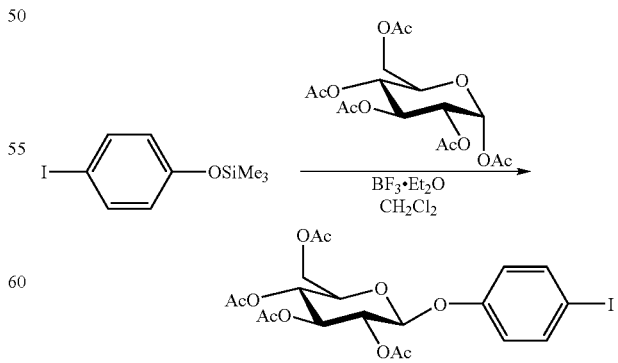

To a solution of 1-iodo-4-thrimetilsilyloxybenzene (0.400 g, 1.37 mmol) in dichloromethane (5 ml), was added dropwise under a nitrogen atmosphere a solution in dichloromethane (6 ml) of glucose pentaacetate (0.588 g, 1.51 mmol), then the BF$_3$*Et$_2$O (1.37 ml).

After about 15 hours, the reaction mixture was diluted with water, extracted with ethyl acetate, and the organic phase washed with a n aqueous saturated solution of NaHCO$_3$ (3×100 ml). The organic phase was dried on anhydrous sodium sulfate, and the solvent was distilled at reduced pressure.

The residue was crystallized from methanol (white solid, 0.681, yield 90%).

$^1$HNMR (CDCl$_3$, 400 MHz) δ 2.02 (s, 3H), 2.03 (s, 3H), 2.04 (s, 3H), 2.06 (s, 3H), 3.81-3.87 (m, 1H), 4.14 (dd, 1H J=12.3, 2.4 Hz), 4.26 (dd, 1H, J=12.3, 5.4 Hz), 5.03 (dl, 1H, J~8 Hz) 5.14 (tl, 1H, J~9 Hz) 5.21-5.31 (m, 2H), 6.75 (dl, 2H, J~9 Hz), 7.57 (dl, 2H, J~9 Hz).

Example 4.2

Synthesis of (2,2'-bithiophen-5-yl)-4-[2,3,4,6-tetra-O-acetyl-β-D-glucopiranosyl]benzene (DTZ)

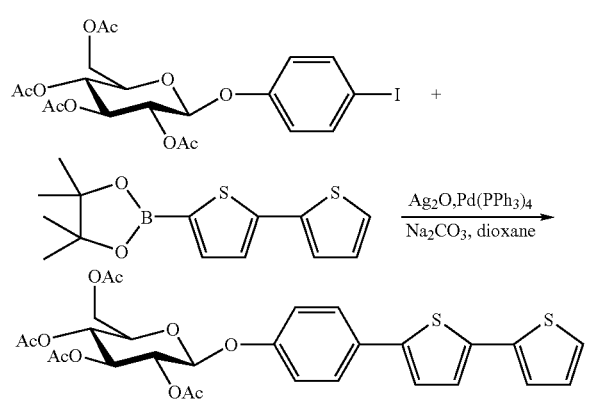

To a solution of 1-iodo-4(2,3,4,6-tetra-O-acetyl-β-D-glucopyranosyl)benzene (0.155 g, 0.28 mmol) and 5-(4,4,5,5-tetramethyl-1,3,2-dioxaborolan-2-yl)-2,2'-bitiofene (0.102 g, 0.35 mmol) in anhydrous dioxane (5 ml), were added under a nitrogen atmosphere, Na$_2$CO$_3$ (0.026 g, 0.27 mmol), Ag$_2$O (0.063 g, 0.27 mmol) and Pd(PPh$_3$)$_4$.(0.011 g, 0.01 mmol).

The reaction mixture was refluxed (at 80° C.) for 4 hours, then cooled to room temperature. The solvent was removed at reduced pressure and the residue was diluted with an aqueous saturated of NH$_4$$^+$Cl$^-$. The resulting mixture was extracted with ethyl acetate and the organic layer dried on anhydrous sodium sulfate. After filtration, the solvent was removed at reduced pressure.

The residue was purified by silica gel column chromatography (petroleum ether/ethyl acetate 6/4). A bright yellow solid was obtained (m.p. 195-196° C., from is dichloromethane/hexane) (0.100 g, 48% yield).

$^1$H NMR (CDCl$_3$, 400 MHz) δ 2.04 (s, 3H9, 2.06 (s, 3H), 2.08 (s, 3H), 2.09 (s, 3H), 3.83-3.91 (m, 1H), 4.18 (dd, 1H J=12.3, 2.4 Hz), 4.30 (dd, 1H, J=12.3, 5.3 Hz), 5.10 (dl, 1H, J~8 Hz), 5.18 (tl, 1H, J~9 Hz), 5.25, 5.35 (m, 2H) 6.97 (dl, 2H, J~9 Hz), 7.02 (dd, 1H, J=3.6, 5.1 Hz), 7.12 (d, 1H, J=3.8 Hz), 7.13 (d, 1H, J=3.8 Hz), 7.18 (dd, 1H, J=3.6, 1.1), 7.22 (dd, 1H, J=5.1, 3.6) 7.52 (dl, 2H, J~9 Hz).

Example 5

Synthesis of the 6-{4-[2,2']bithyophen-5-yl-phenoxy}hexyl ester of the (2S)-2-tert-buthoxycarbonylamino-3-phenylpropyonic acid (DTA)

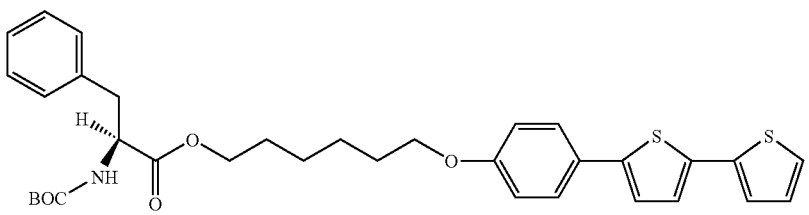 [SMILES: CC(C)(C)OC(=O)N[C@@H](Cc1ccccc1)C(=O)OCCCCCCOc1ccc(-c2ccc(-c3cccs3)s2)cc1]

Example 5.1

Synthesis d of 6-(4-iodophenoxy)hexan-1-ol

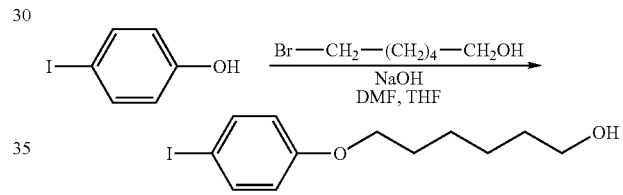

A solution of NaOH (0.327 g, 8.18 mmol) and 4-iodophenol (1.5 g, 6.82 mmol) in 7.5 ml of DMF and 3.5 ml of THF was stirred at room temperature for 15 minutes. Then bromohexanol (1.482 g, 8.18 mmol) was added and the reaction mixture was warmed at 60° C. When the reaction is over, water was added (15 ml) and the mixture was extracted with ethyl acetate. The organic phase was dried over anhydrous sodium sulphate and after filtration the solvent was removed at reduced pressure. The product was isolated by silica gel column chromatography using a mixture of ethyl acetate: dichloromethane 3:7 as eluant. A white solid was obtained (1.509 g, yield 69%).

Example 5.2

Synthesis of 6-(4-iodophenoxy)hexyl ester of 2-tert-butoxycarbonylamino-3-phenyl-propionic acid

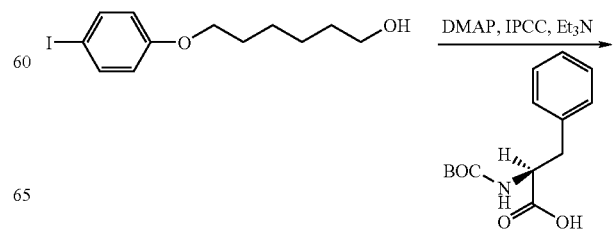

-continued

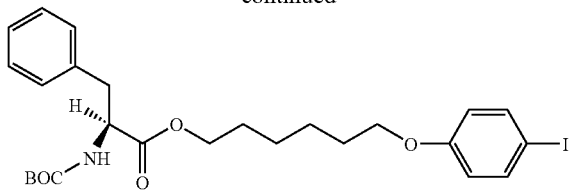

Triethylamine (0.217 g, 2.7 mmol) and DMAP (0.059 g, 0.48 mmol) were added under a nitrogen atmosphere to a solution of 6-(4-iodophenoxy)-hexan-1-ol (0.700 g, 2.19 mmol) and N-BOC phenylalanine (0.650 g, 2.45 mmol) in dry dichloromethane (16 ml). The resulting mixture was cooled slowly to 0° C., and IPCC (0.345 g, 2.86 mmol) was added dropwise. After stirring at 0° C. for 1 hour, the reaction was quenched by addition of water and small amounts (5 ml) of saturated aqueous solutions of ammonium chloride and sodium chloride.

The mixture was extracted with dichloromethane (3×30 ml), and the organic layer dried over anhydrous sodium sulfate. After filtration, the solvent was removed at reduced pressure. The crude product was purified by silica gel column chromatography using petroleum ether/ethyl acetate 8.5/1.5 as eluant. A colourless thick oil was recovered (0.919 g, 72% yield).

$^1$HNMR (CDCl$_3$, 400 MHz) δ 1.39 (s, 9H), 1.26-1.48 (m, 4H), 1.58 (quintet, 2H, J=6.8 Hz), 1.73 (quintet, 2H, J=6.8 Hz), 2.98-3.10 (m, 2H), 3.87 (t, 2H, J=6.8 Hz), 4.01-4.12 (m, 2H), 4.53 (bq, 1H, J~7 Hz), 4.95 (bd, 1H, J~7 Hz), 6.63 (tl, 2H, J~8 Hz), 7.09 (dl, 1H, J~8 Hz), 7.17-7.29 (m, 3H), 7.50 (dl, 2H, J~8 Hz).

Example 5.3

Synthesis of 6-{4-[2,2']bithiophen-5-yl-phenoxy}hexyl ester of (2S)-2-tert-butoxycarbonylamino-3-phenylpropionic acid

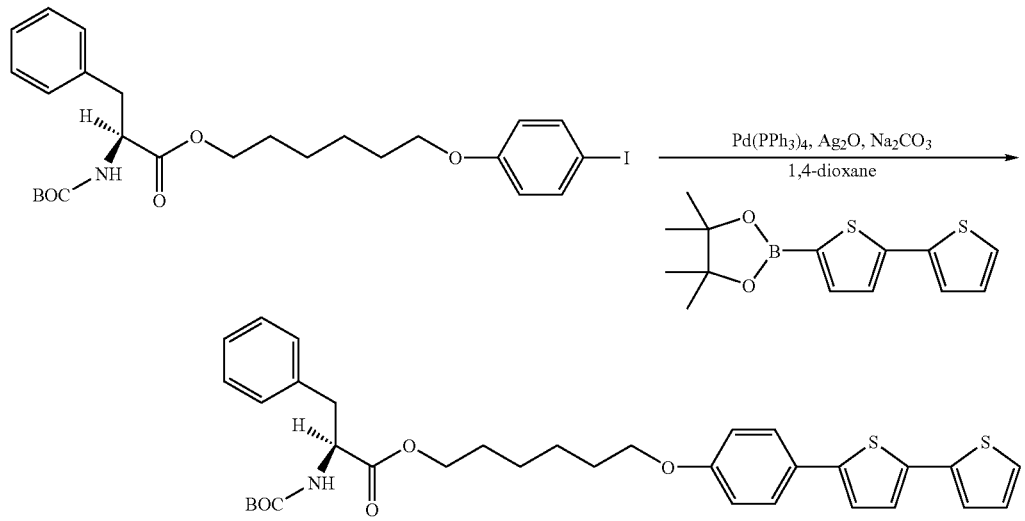

A solution of 5-(4,4,5,5-Tetramethyl-1,3,2-dioxaborolan-2-yl)-2,2'-bithiophene (0.165 g, 0.57 mmol), dissolved in dry dioxane (3 ml), was added to a solution of the 6-(4-iodophenoxy)hexyl ester of the 2-tert-butoxycarbonylamino-3-phenyl-propionic acid (0.300 g, 0.51 mmol) under a nitrogen atmosphere. Anhydrous sodium carbonate (0.055 g, 0.51 mmol), silver oxide (0.119 g, 0.51 mmol) and the catalyst Pd(PPh$_3$)$_4$ (0.018 g, 0.015 mmol) were then added and the resulting mixture was stirred at 80° C. for 15 hours. The reaction was quenched by adding an aqueous saturated solution of ammonium chloride (7 ml). The mixture was extracted with dichloromethane (3×20 ml), and the organic phase dried over anhydrous sodium sulfate. After filtration the solvent was removed at reduced pressure. The crude product was purified by silica gel column chromatography using petroleum ether/ethyl acetate 8/2 as eluant, then by crystallization from dichloromethane (yellow solid, m.p. 103.0-104° C., 0.236 g, yield 74%).

$^1$HNMR (CDCl$_3$, 400 MHz) δ 1.42 (s, 9H), 1.32-1.53 (m, 4H), 1.63 (quintet, 2H, J=6.8 Hz), 1.79 (quintet, 2H, J=6.8 Hz), 3.02-3.15 (m, 2H), 3.98 (t, 2H, J=6.8 Hz), 4.06-4.16 (m, 2H), 4.57 (bq, 1H, J~7 Hz), 4.99 (bd, 1H, J~7 Hz), 6.90 (dl, 2H, J~8 Hz), 7.10 (d, 1H, J=3.7 Hz) 7.11 (d, 1H, j=3.7 Hz) 7.01 (dd, 1H, J=5.1, 3.6 Hz), 7.12-7.15 (m, 1H), 7.17 (dd, 1H, J=3.6, 1.2 Hz) −7.20 (dd, 1H, J=5.1, 1.1), 7.22-7.31 (m, 3H) 7.51 (dl, 2H, J~8 Hz)

$^{13}$CNMR (CDCl$_3$, 125.7 MHz) δ 25.60, 25.67, 28.27, 28.39, 29.05, 38.43, 54.43, 65.28, 67.80, 79.83, 114.83, 122.54, 123.30, 124.06, 124.52, 126.74, 126.85, 126.94, 127.77, 128.47, 129.28, 135.57, 136.03, 137.56, 143.15, 155.07, 158.73, 171.98.

Example 6

Fabrication of Organic Thin Film Transistor Based on PTO

A OTFT device was fabricated by using a rectangular shaped p-doped silicon wafer (resistivity: 0.1-1 Ω/cm) coated by a 300 nm thick SiO$_2$ thermal oxide.

The gate contact was realized by removing the silicon dioxide in a small region of the dielectric layer by using a diamond tip and subsequently covering this region with thermally evaporated gold. Then, the substrate was rinsed with triple distilled water, acetone and triple distilled water and finally dried in a nitrogen stream to remove any kind of dust or impurity.

The organic semiconductor thin film was then deposited onto the Si/SiO$_2$ substrate prepared as described above; to improve the adhesion, the elicited substrate is functionalized with hydrophobic moieties by exposition to 1,1,1,3,3,3-hexamethyldisilazane (HMDS) saturated vapours over night. This treatment allows to modify the SiO$_2$ surface chemistry by making it partially idrophobic as the OH groups, naturally present on the SiO$_2$, are substituted by methyl groups. The polarity of the substrate, affects the morphological and structural property of the films and it is well known that the HMDS, promoting the phase segregation of the polymeric systems at interface with the dielectric layer, allows the arrangement of the polymeric chains in a better ordered structure.

Organic materials were then deposited by using different techniques such as drop casting, spin coating, thermal evaporation and Langmuir-Schäfer.

Finally, source and drain electrodes were defined on the organic layer by thermal evaporation of gold through a shadow mask. The channel length and width were respectively 200 μm and 4 mm. During the evaporation the small portion of the substrate, not covered by SiO$_2$, was also covered with gold in order to define the ohmic contact gate.

Example 6.1

Organic Thin Film Fabrication

The molecules employed as active layer in the OTFT bilayer architecture fabricated according to the present invention are phenylene-thienylene oligomers. The PTO oligomer is characterized by two octyloxy chains while six carbon atom alkoxy chains linked through an ester bond to the carboxylic group of a N-BOC protected L-phenylalanine molecule, are the PTA substituents. PTO and PTA are both soluble in common organic solvents such as tetrahydrofuran, chloroform and dichloromethane and so they can be processed by solution deposition techniques such as drop casting, spin-coating and Langmuir-Shäfer.

Such deposition techniques allow to obtain thin films with different morphological and structural properties and so with different electrical properties.

The drop casting technique allows the formation of non homogeneous film, but the slow evaporation of the solvent improves the self-assembling properties of the oligomeric chains forming the crystalline grains. On the other hand, the spin coating procedure leads to the formation of uniform films, but the fast evaporation of the solvent hampers the natural packing of the chains in the grain structures. The Langmuir-Shäfer technique, called "layer by layer", allows to deposit pre-oriented Langmuir-Shäfer transfers of the oligomers on Si/SiO$_2$ to give extremely ordered film.

For the above mentioned deposition techniques, PTO and PTA were dissolved in chloroform solution. The drop casting thin film deposition was carried out by depositing 50 μL of the oligomer solutions (0.3-0.5 mg/mL) on the Si/SiO$_2$ subsequently allowing the solvent evaporation in a nitrogen stream. The spin coating depositions were carried out, in a nitrogen atmosphere, by depositing on the substrate a volume of 50 μL of the solution with the same concentration and setting a rotating velocity of 2000 rpm for 40 seconds. As to the Langmuir-Shäfer (addressed in the following as LS) depositions is concerned a PTO solution was realized in chloroform with a concentration of 0.275 mg/mL while for PTA the solution concentration was 0.279 mg/mL.

In order to obtain LS transfer at the water-air interface a suitable volume of solution was spread on the sub-phase surface and then we waited for 15 min to allow the complete evaporation of the solvent. The volumes of solution spread onto the sub-phase surface was 600 μL for PTO and 200 μL for PTA.

After having spread the solution on the sub-phase, the floating film at the air-water interface was slowly compressed by means of two floating barriers moved by an electric engine at a speed of 10 mm/min while keeping the surface pressure at 20 mN/m for both the oligomers of PTO and PTA.

The surface pressure used to perform the depositions has been chooser by extrapolation from the Langmuir isotherm relative to the molecule under investigation (FIG. 3). It corresponds to the initial value of the straight line of the isotherm which is relevant to the condensate phase. In this zone of the curve we are sure of the formation of preoriented LS transfers.

The trend of the isotherm curve for PTA is similar to that of PTO shown in FIG. 3, so both depositions were carried out at the same surface pressure value. PTO Langmuir isotherm shows a gas phase for $\Pi<1$ mN/m, a liquid phase for $1<\Pi<20$ mN/m and a condensate phase in the straight line portion of the curve for $\Pi>20$ mN/m.

From the study of the isotherm curve it was derived that, the surface pressure able to keep the better structural order of the molecules is 20 mN/m while at value larger then 50 mN/m the film collapses. The isotherm curve evidences that a fast reduction of the area per molecule occurs even if the surface pressure in lowered of few mN/m, this being an indicative parameter of the self-assembling properties of the amphiphilic molecules.

The molecules deposition was performed on pristine Si/SiO$_2$ and on the same substrates that were previously transformed into hydrophobic ones by a treatment over night in a desiccator with saturated vapour of 1,1,1,3,3,3-hexamethyldisilazane (HMDS). This treatment allows to modify the surface of the silicon dioxide and make it partially apolar since the OH groups naturally present on the SiO$_2$ are substituted by methyl groups.

The polarity of the substrate affects the morphological and structural properties of the thin films and therefore such a parameter has to be continuously monitored in order to understand the growning mechanisms of the supramolecular structures. As to this is concerned, it is well-know that the HMDS promotes the phase segregation of the polymeric system at interface with dielectric layer and allows the arrangement of the polymeric chains in a better ordered structure.

Example 7

OTFT Devices Electrical Characterization

Measurement of the current-voltage characteristics by means of semiconductor parameter analyzer such as the Agilent-45155C.

Example 7.1

Figure 4:
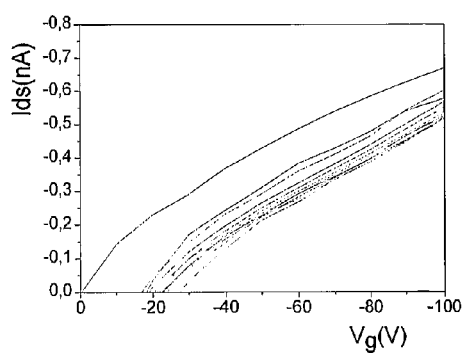
FIG. 4 is a diagram of a characteristic curve obtained from an organic thin film transistor fabricated with a first deposition technique of the compounds.
Figure 5:
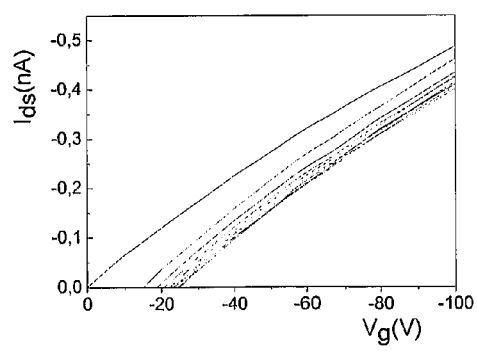
FIG. 5 is a diagram of a characteristic curve obtained from an organic thin film transistor fabricated with a second deposition technique of the compounds.

I-V Characteristic Curves of the OTFTs Fabricated by Using drop Casting and Spin Coating Techniques OTFT devices based on PTO deposited by drop casting and spin-coating on Si/SiO$_2$ (with and without HMDS treatment) do not exhibit any field-effect modulation. Indeed, current-voltage characteristics shown in FIGS. 4 and 5 point out the absence of a modulated current with the gate voltage and hence these devices have a resistive like behaviour.

Example 7.2

OTFTs Characteristic Curves Fabricated by Using LS Deposition Technique

OTFT devices fabricated by using LS deposition technique show the typical field effect transistor behavior. As an example the I-V characteristic curve of the OTFT devices composed of 5 LS transfers of PTO at 20 mN/m (FIG. 6A e 6B) and 12 mN/m (FIG. 7) are reported.

Example 7.2.1

I-V Characteristics of the OTFT at Different Numbers of LS Transfer

From the analysis of the electrical behavior of the devices having different LS transfer of PTO on $Si/SiO_2$ and on the same substrates previously hydrophobized trough HMDS treatment it is possible to get information on what is the thickness of active layer that guarantees the best electrical performances. The field effect mobility values and the $I_{on}/I_{off}$ ratio for the OTFT devices composed of a different number of LS transfers of PTO ranging from 5 to 30 and deposited on hydrophobized substrates are reported in the following Table 1

TABLE 1

| number of LS transfers | $\mu_{FET}$ (cm$^2$/Vs) | $I_{on}/I_{off}$ |
|---|---|---|
| 5 | $2 * 10^{-5}$ | 45 |
| 10 | $6 * 10^{-5}$ | 24 |
| 15 | $3 * 10^{-4}$ | 93 |
| 20 | $1.5 * 10^{-4}$ | 41 |
| 30 | $1 * 10^{-4}$ | 54 |

From the data reported in Table 1 it can be noted that the substrates constituted of 15, 20 and 30 transfers LS exhibit very similar mobility values falling in the range $(1-3)*10^{-4}$ cm$^2$/V sec and for a number of LS transfers lower than 15 the mobility decreases by an order of magnitude. This effect is probably due to the fact that the substrate coverage is incomplete after the deposition of a certain number of LS transfers. Besides, the $I_{on}/I_{off}$ ratio decreases when the thickness increases, since the off current, expression of the three-dimensional conduction of the bulk of the organic semiconductor, raises.

Example 7.2.2

Figure 8A:
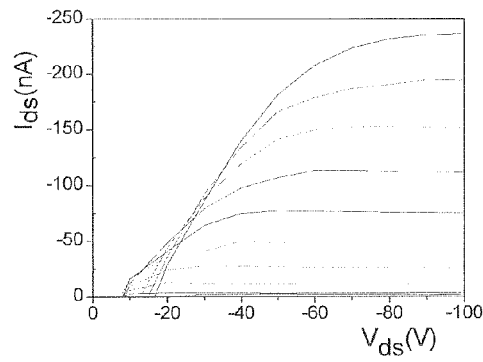
FIGS. 8A and 8B are diagrams of the characteristic curves obtained from organic thin film transistors fabricated with the preferred deposition technique employing the PTO to obtain a film comprising 15 LS transfer, after the deposition of an adhesion promoter.
Figure 8B:
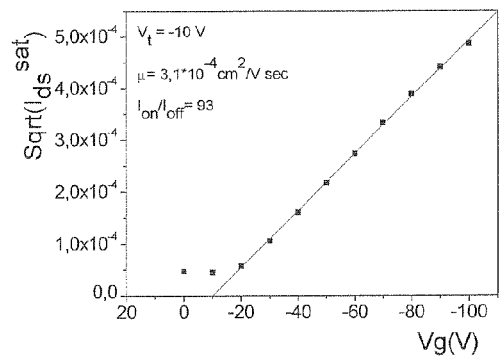
Figure 9A:
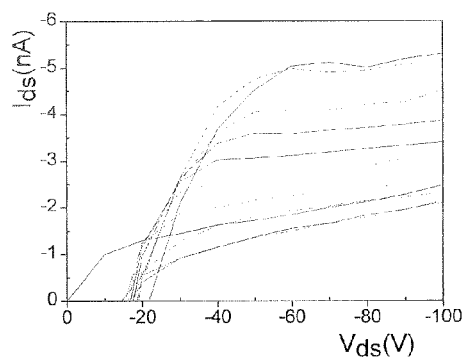
FIGS. 9A and 9B are diagrams of the characteristic curves obtained from organic thin film transistors fabricated with the preferred deposition technique employing the PTO to obtain a film comprising 15 LS transfer, with no adhesion promoter.
Figure 9B:
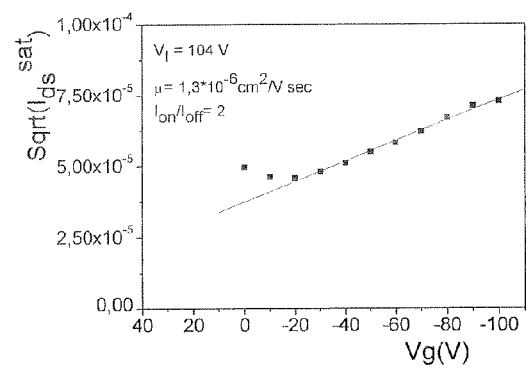

I-V Characteristic Curves of the OTFT Depending on the Substrate Pre-Treatment As an example, the I-V electrical characteristics of two devices with active layer constituted of 15 LS transfers deposited on $Si/SiO_2$ previously pre-treated with HMDS (FIGS. 8A and 8B), or directly on pristine $SiO_2$ (FIGS. 9A and 9B) are reported.

A comparison of the figures of merit of the devices in the elicited figures points out the relevance of the adhesion promoter regarding the formation of highly order structures, as its macroscopic effect is an improvement of the electric properties of the thin film. Indeed, the device based on PTO oligomers deposited on previously hydrophorized $Si/SiO_2$ shows mobility values as high as 3.1 cm$^2$/Vs and $I_{on}/I_{off}$ of 93. OTFT devices to fabricated depositing PTO molecule directly on $Si/SiO_2$ shows mobility value of $1.3*10^{-6}$ cm$^2$/Vs while $I_{on}/I_{off}$ is 2. On the basis of these observations OTFT based on PTO with thickness equal to 15 Ls transfers will be used to perform the gas sensing measurements described in the following.

Example 8

Preparation of a Thin-Film Transistor Based on PTA

Figure 10:
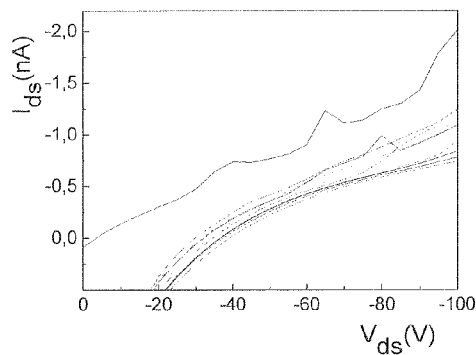
FIG. 10 is a diagram of the characteristic curves obtained from a organic thin film transistors fabricated with the preferred deposition technique employing the PTA to obtain a film comprising 15 LS transfer, with no adhesion promoter.
Figure 11:
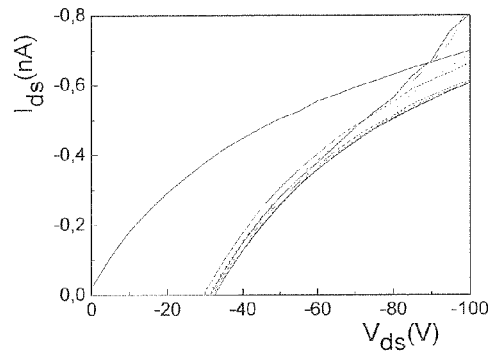
FIG. 11 is a diagram of the characteristic curves obtained from organic thin film transistors fabricated with the preferred deposition technique employing the PTA to obtain a film comprising 15 LS transfer, after the deposition of an adhesion promoter.

OTFT devices based on a 15 LS transfers of PTA do not show satisfying results both when deposited on hydrophilic and hydrophobic substrates as it can deduced from the electrical characteristics shown respectively in FIGS. 10 and 11. Indeed such devices do not exhibit the desired field-effect amplified current at negative gate bias. This behaviour is probably due to the steric hindrance of the aminoacidic groups of the PTA that obstructs the chains packing in the film structure worsening its conductive properties.

Example 8.1

Preparation of Thin Film Transistor Employing a PTO/PTA Bilayer

The structural order in the organic semiconductor region in contact with the silicon dioxide affects the electrical performances of the OTFT since this is the region where the field-effect is confined. This suggests to deposit a few LS transfers of PTO, that show good electrical transport properties, in direct contact with $Si/SiO_2$ substrates and subsequently overlie on it some LS transfers of PTA. The current-voltage characteristics for different number of LS transfers show, in fact, current amplification with the gate bias for all the devices fabricated on hydrophobized $SiO_2$. The figure of merits and the corresponding thickness value for each device are listed in table 2.

TABLE 2

| Number of LS trasfers | $\mu_{FET}$ (cm$^2$/Vs) | $I_{on}/I_{off}$ |
|---|---|---|
| 5 PTO + 5 PTA | $4.1 * 10^{-5}$ | 2.5 |
| 10 PTO + 5 PTA | $1.9 * 10^{-4}$ | 48.3 |
| 20 PTO + 5 PTA | $1.3 * 10^{-4}$ | 68.5 |
| 30 PTO + 5 PTA | $2 * 10^{-4}$ | 4.3 |

Figure 12A:
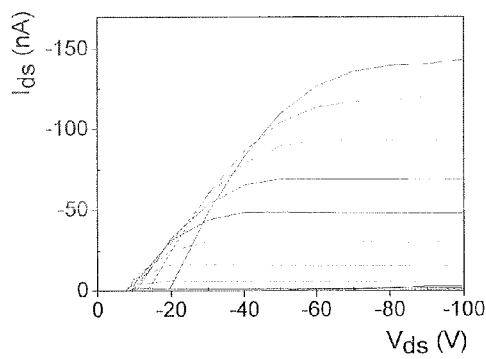
FIGS. 12A and 12B are diagrams of the characteristic curves obtained from organic thin film transistors fabricated with the preferred deposition technique employing the PTO and the PTA to obtain a film comprising 10 LS transfer of PTO and 5 LS transfer of PTA.
Figure 12B:
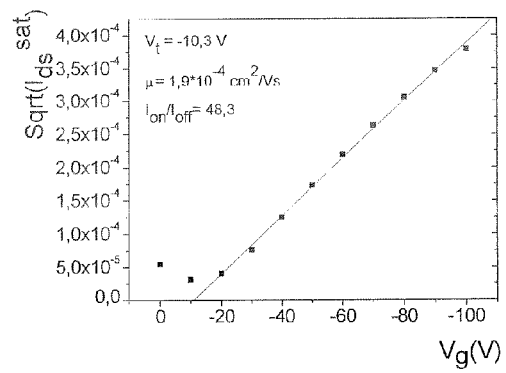

Also for these devices the mobility and $I_{on}/I_{off}$ values followed the same trend seen for the PTO one. The I-V characteristics curve, along with the mobility and $I_{on}/I_{off}$ values, for the OTFT based on 15 LS transfer are reported in FIGS. 12A and 12B. Such device shows a mobility of $9*10^{-4}$ cm$^2$/Vs and an $I_{on}/I_{off}$ ratio of 48. On the basis of these results the sensor holding the optimized characteristics is constituted of 10 PTO LS transfer to (first layer) and 5 LS transfer of PTA (second layer). In this fashion it is possible to combine the conductivity properties of the PTO oligomers with those of enantioselective recognition that are typical of PTA.

Example 9

Calibration of OTFT Devices—Realization of an Experimental Set-Up for the Acquisition and Digitalization of the Sensor Responses Upon Exposures to the Enantiomers Vapours of a Chiral Compound, Citronellol in Fact, at Different Concentrations Controlled concentration flows of citronellol vapours have been obtained flowing nitrogen in apposite bubbler containing the liquid analyte. The citronellol concentration in the nitrogen flow can be esteemed by assuming that the molar fraction of the analyte in the gas phase is the ratio between its partial pressure and the total pressure, i.e. the atmospheric pressure. Nevertheless, to assume that the partial pressure of the citronellol in nitrogen flow correspond to its saturated vapor can result in an over estimation error since the saturation may not be completed.

A calibration of the gas sensing system through gas-cromatographic analysis of the gaseous mixture is therefore necessary to establish a correct relationship between the vapor pressure of the citronellol in nitrogen flow and its saturated vapor.

Such relationship is the ratio between the heights (or equivalently between the areas) of the chromatographic peaks registered by injecting a known quantity of vapor taken from a bubbler and the same quantity coming from the head space of a vial (closed with a punched silicon septum) containing a small volume of citronellol pure liquid.

In the latter system it is necessary that the liquid-vapor equilibrium is reached. This generally takes several hours. The concentration of the citronellol in the saturated vapor, estimated according to this procedure, is 86 ppm at 18.5° C. (corresponding to the temperature of the thermostatic bath in which the bubblers are immersed). The vapour aliquots in both cases are collected through gas-tight syringe equipped with a closing valve.

The calibration previously reported was performed with a Shimadzu GC-17AAF gascromatograph equipped with a digital data acquisition interface connected to a PC operated by the Cromatoplus software, endowed with a split-splittless injector, a fused silica capillary column of 30 m long and with a diameter of 0.25 m as weòò as with a 0.25 μm thick carbowax (polydimetilglicol) stationary phase and a flame ionization detector (FID) fed with hydrogen/air. The elution was realized employing the following experimental conditions:

injection temperature: 220° C.;
FID temperature: 250° C.;
column temperature: 45° C. (3 min)-220° C.; rate 5° C./min.;
flow rate 12 cm/sec;
splittless injection modality.

The average values of the chromatographic peak heights and the relative retention times are summarized in table 3 and they refer to three replicates for each of the three analytes.

TABLE 3

| Parameter | Saturated vapour (vial) | (+) citronellol | (−) citronellol |
|---|---|---|---|
| $t_R$ (min) | 36.13 | 36.20 | 36.24 |
| height (u.a.) | 5063 ± 970 | 2894 ± 629 | 3116 ± 412 |

The experimental results were compared by means of a statistical test in order to establish whether they are significantly different or not.

Example 10

Gas Sensing Measurements and Enantiomeric Discrimination

The exposition to known concentrations of citronellol vapours in nitrogen, determined as reported in the previous example, of both devices bearing as sensitive layer the achiral ologomer PTO as well as devices with a double layer (bilayer) PTO-PTA, allowed to compare the responses of a sensor not able to install selective interactions with the different enantiomers and a potentially enantioselective sensor respectively.

Nitrogen was used as reference gas to establishing a base-line level while gas sensing measurements were performed by delivering the citronellol vapours, diluted to different concentration in nitrogen, on the device and measuring an almost instant variation of the chemical atmosphere over the active layer.

Gas sensing measurements was carried out by measuring $I_{ds}$-$V_g$ trans-characteristics upon exposure of the devices to the sole nitrogen flux and when, immediately after, the sensor is exposed, at the same flow rate (200 ml/min), to a controlled concentration flow of citronellol.

In particular all the measurements were carried out by fixing the source-drain bias at $V_{ds}$=−50V (saturation regime) and by sweeping the gate bias between $V_g$=+50 e $V_g$=−100V. Overall the exposure time of the sensor to the volatile analyte is of 45 seconds. Before starting the $V_g$ run, and therefore before the measurement of each trans-characteristic, the device is conditioned by exposure to the analyte atmosphere for 45 s. In such conditions the $I_{ds}$ current increases with $V_g$ and this is the evidence that a field-effect is occurring that turns out into an amplification of the current flowing in the transistor. Nevertheless, as the device is exposed to a citronellol vapours, the recorded current increase is lower compared to that obtained in the presence of the sole nitrogen; this is due to the interaction of citronellol molecules in the gas phase with the thin film. This phenomenon is responsible for the chiral discrimination as the enantiomer capable to install the stronger interaction determines a stronger variation of the device electrical parameters and this translates into a higher reduction of the source drain current The macroscopic effect of the interaction can be indeed seen form the gap between the trans-characteristics measured when the device is exposed to a citronell vapours with respect to the base line. As an example, one of the responses of the achiral PTO-OTFT sensor is reported (FIGS. 13A and 13B) where the lower curve pertains to the trans-characteristic in nitrogen flux and the upper curve follows the trend of the current during the exposition to the citronellol vapours.

The current changes ΔI (device response) indicated in the Figure is the difference calculated at $V_g$=−100V. The measurements are relevant to a concentration of 2.55 ppm for both R(+) and S (−) citronellol enantiomers in nitrogen.

Both the figures show that the PTO based devices deliver similar responses for both the citronellol enantiomars impairing the possibility of any enantioselective recognition. As the concentration of the analyte is increased an increase of the sensor response could be seen, as it can be seen in FIGS. 13C and 13D, where the responses, for both the enantiomers are reported at a citronellol concentration of 30.6 ppm. Also in this case no difference can be seen between the two responses to the two isomers: the sensor based on the achiral oligomer in fact is not chemically capable to establish enantioselective interactions with the two citronellol enatiomers.

It is important to outline that the OTFT sensor ΔI response variation is also a function of the $V_g$ bias applied. In particular when $V_g$ holds a low (absolute) value, the response is lower then when the devices is biased at $V_g$=−100 V. This translates into a higher sensitivity amplified (even of one order of magnitude) of the OTFT in the charge accumulation regime i.e. for $|V_g|>|-30V|$. This discovery opens interesting perspectives in the use of OTFT sensors as "sensing-switches"

On the other hand, the OTFT based on the PTA oligomer shows different responses depending on weather it is exposed to one or the other enantiomer. The experimental results, in this case, point out that the chiral sites of the amminoacid give enatiomeric recognition capabilities to due to the different interaction of the optically active PTA with the (+) and (−) citronellol forms (FIGS. 14A-14D).

Figure 14A:
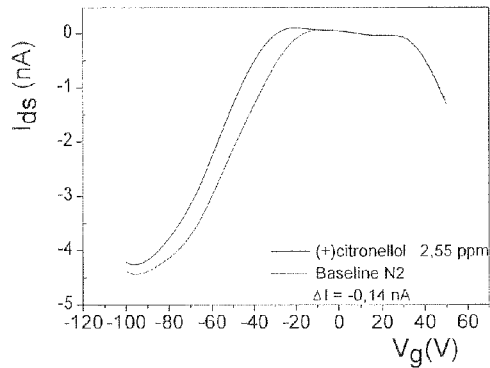
FIGS. 14A and 14B illustrate some significant characteristic curves of the experimental evidence of the gaseous analytes detection, for the enantiomeric compounds at a first concentration level. These curves were obtained using an organic thin film transistor including an LS transferred layer of PTO and an LS transferred layer of PTA.
Figure 14B:
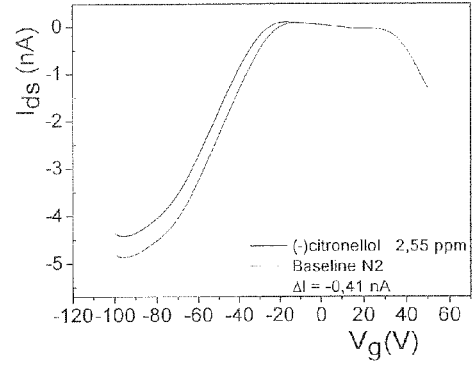
Figure 14C:
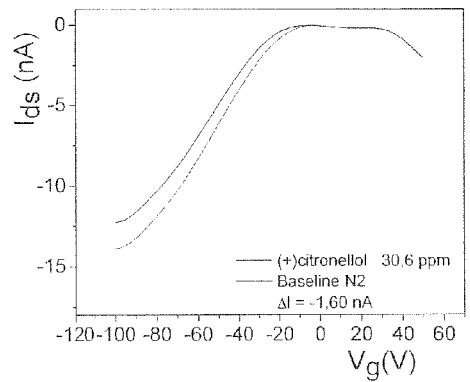
FIGS. 14C and 14D illustrate some significant characteristic curves of the experimental evidence of the gaseous analytes detection, for the enantiomeric compounds at a second concentration level. These curves were obtained using an organic thin film transistor including an LS transferred layer of PTO and an LS transferred layer of PTA.
Figure 14D:
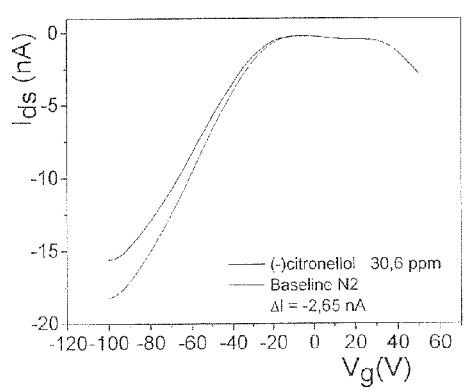
Figure 14E:
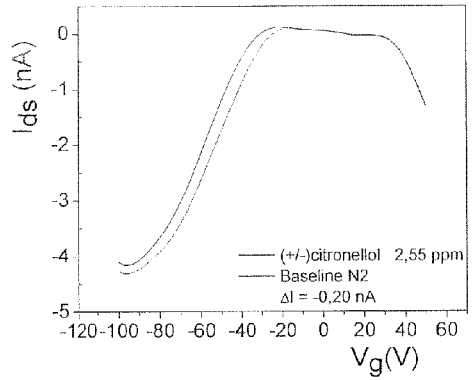
FIGS. 14E and 14F illustrate some significant characteristic curves of the experimental evidence of the gaseous analytes detection, comprising the racemic mixture of the same compound at a first and at a second concentration level. These curves were obtained using an organic thin film transistor including an LS transferred layers of PTO and an LS transferred layer of PTA.
Figure 14F:
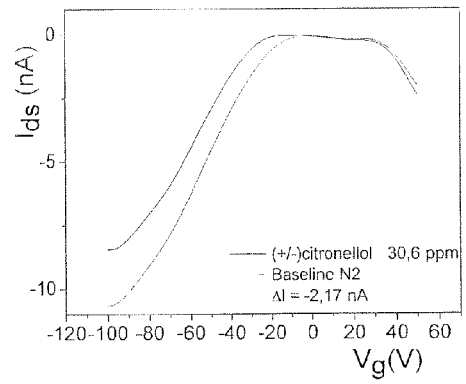

Also in this case the response increases with the concentration and with $V_g$ as it is evident by comparing FIGS. 14A and 14B (2.5 ppm) and the corresponding FIGS. 14C and 14D (concentration: of 30.6 ppm). The chiral sensor exposed to a racemic mixture R(+)/S(−) of citronelloll shows a response that has an intermediate value as compared to those of the two enantiomens. As an example the two responses relevant to the exposure of the device to a racemic mixture of 2.55 and 30.6 ppm are reported in FIGS. 14E and 14F respectively.

Example 11

Fabrication of Transistors with Double Layer Thin Film PTO/PTZ (Bilayer)

Figure 15:
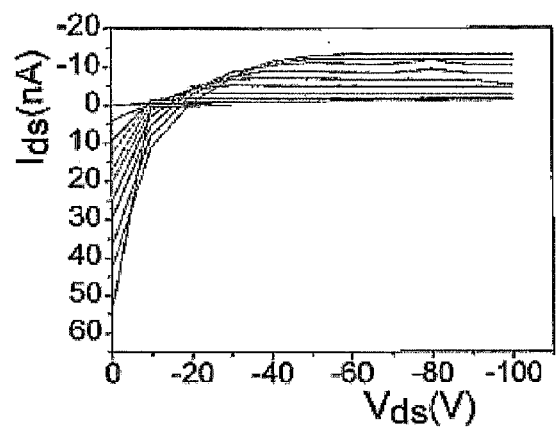
FIG. 15 illustrates a significant characteristic curve of an organic thin film transistor including an LS transferred layer of PTO and an LS transferred layer of PTZ.

On the basis of the results reported in example 8.1, a bilayer OTFT device has been fabricated with an active layer formed by 10 LS PTO transfers (first layer) and of 5 LS PTZ transfers (second layer). The I-V characteristic curves of such device are illustrated, as an example, in the $V_{ds}/I_{ds}$ diagram of FIG. 15.

Example 12

Enantioselective Discrimination Measurements by Using PTO/PTZ Device

The device has been realized following the description in the Example 11 and it has been tested following the procedure already illustrated in the Example 10.

Figure 16A:
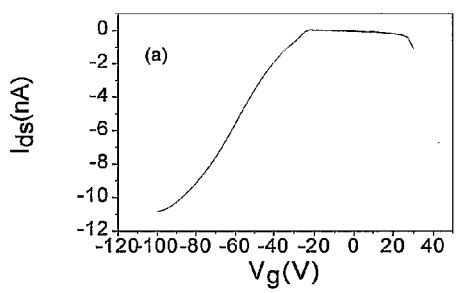
FIGS. 16A-16C illustrate some significant characteristic curves of the experimental evidence of the gaseous analytes rivelation, comprising the enantiomeric compounds. These curves were obtained using an organic thin film transistor including an LS transferred layer of PTO and an LS transferred layer of PTZ.

Also in this case the measurements were performed by measuring $I_{ds}$-$V_s$ trans-characteristics when the device is exposed to the sole nitrogen flux and, soon after, the sensor is exposed to a flux of the same rate (200 mL/min) with a controlled concentration of citronellol. The exposure of the sensor PTO/PTZ to the nitrogen flow produced the curve reported in FIG. 16A.

Figure 16B:
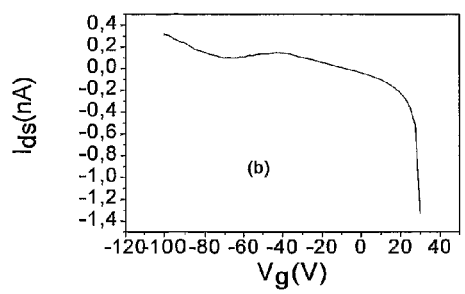
Figure 16C:
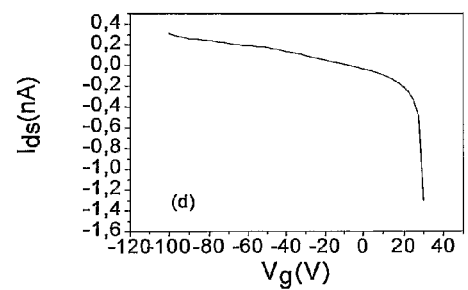

From the curves reported FIGS. 16B and 16C it can be noted that the OTFT sensor based on the PTO oligomer showed different responses to the two citronellol enantiomers. Also in this case, as it happens to the PTO/PTA device, the experimental results expressed by the trans-characteristics (measured at a concentration of 30.6 ppm) point out the enantioselective recognition capabilities due to a different interaction of the optically active PTZ of PTZ/PTO with the (+) form of citronellol (FIG. 16B) and (−) form of citronellol (FIG. 16C).

The invention claimed is:
1. A compound having the following formula (I)

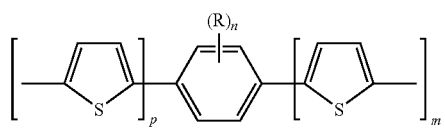

(I)

wherein
n is a whole number from 1 to 4
m and p are whole numbers from 0 to 5, equal or different from each other, provided that at least one among m and p are different from 0;

R is
an alkoxy chain $C_1$-$C_{12}$, bearing an aminoacid in optically active form as substituent or
a monosaccharide unit;
when n is different from 1, R groups may be the same or different from each other.

2. The compound according to claim 1, characterized in that R is a 6 carbon atom alkoxy chain bearing an optically active aminoacid as substituent.

3. The compound according to claim 1, characterized in that said aminoacid is chosen among natural D or L-aminoacids.

4. The compound according to claim 1, characterized in that the above mentioned monosaccharide unit is glucose.

5. The compound according to claim 1, characterized in that said amino acid is D or L-phenylalanine.

6. The compound according to claim 1, selected among
1,4-bis[5-(2,2'-bithienyl)]2,5-bisoctyloxybenzene (PTO);
6-{2,5-bis-[2,2']bithiophenyl-5-yl-4-[6-(2-tert-butoxycarbonylamino-3-phenyl-propionyloxy)-hexyloxy]-phenoxy}-hexyl ester of the 2-amino-3-phenyl-propionic aid;
6-{2,5-bis-[2,2']bithiophenyl-5-yl-4-[6-(2-tert-butoxycarbonylamino-3-phenyl-propionyloxy)-hexyloxy]-phenoxy}-hexyl ester of the 2-tert-butoxycarbonylamino-3-phenyl-propionicacid (PTA);
1,4-bis-[2,2']bithiophenyl-2,5-bis-(2,3,4,6-tetra-O-acetyl-β-glucopyranosyl)-benzene (PTZ);
6-(4-[2,2']bithiophen-5-yl-fenoxy)-hexyl ester of the 2-tert-butoxycarbonylamino-3-phenyl-propionic acid (DTA); and
1-[5-(2,2')bithiophen]-4-(2,3,4,6-tetra-O-acetyl-β-D-glucopyranosyl)benzene (DTZ).

7. An organic thin film transistor comprising at least one conducting layer, one dielectric layer, and one semiconducting organic thin film characterized in that said semiconducting organic thin film comprises one or more layers, each of said one or more layers being constituted by at least one compound according to any one of claims 1, 3, 4, 5 or 6.

8. The organic thin film transistor according to claim 7, wherein said semiconductor organic thin film comprises at least two of said layers, realized by different compounds.

9. The organic thin film transistor according to claim 7, wherein said semiconducting organic thin film comprises at least one organic layer according to claim 1 and at least one organic layer according to claim 1 in optical active form.

10. The organic thin film transistor according to claim 7, wherein the semiconducting organic thin films comprises ten overlapped LS transferred layers, which are made of one of the compounds according to claim 1, and five overlapped LS deposited layers made of one of the compounds according to claim 1 in optical active form.

11. A device for gaseous analytes comprising a sensor equipped with the organic thin film transistor according to claim 7, wherein the organic thin film transistor constitutes an active layer to detect toxic gas; the sensor being equipped to measure variation in a chemical atmosphere over the active layer.

12. A device for gaseous analytes comprising an enantioselective sensor equipped with the organic thin film transistor according to claim 7, the enantioselective sensor configured to enable exposure to molecules of citronellol vapours that interact with the one semiconducting organic thin film and thereby enable enantioselective recognition of compounds in gas phase.

13. An integrated circuit comprising one or more than one of the organic thin film transistor according to claim 7.

* * * * *